United States Patent
Mori

(10) Patent No.: US 10,662,443 B2
(45) Date of Patent: May 26, 2020

(54) METHOD FOR PRODUCING ALKANE AND RECOMBINANT MICROORGANISM CAPABLE OF SYNTHESIZING ALKANE

(75) Inventor: Masaaki Mori, Miyoshi (JP)

(73) Assignee: TOYOTA JIDOSHA KABUSHIKI KAISHA, Toyota-shi, Aichi-ken (JP)

( * ) Notice: Subject to any disclaimer, the term of this patent is extended or adjusted under 35 U.S.C. 154(b) by 0 days.

(21) Appl. No.: 14/235,833

(22) PCT Filed: Aug. 15, 2011

(86) PCT No.: PCT/JP2011/068522
§ 371 (c)(1),
(2), (4) Date: Jan. 29, 2014

(87) PCT Pub. No.: WO2013/024527
PCT Pub. Date: Feb. 21, 2013

(65) Prior Publication Data
US 2014/0186915 A1    Jul. 3, 2014

(51) Int. Cl.
C12P 5/02     (2006.01)
C12N 9/02     (2006.01)
C12N 15/81    (2006.01)

(52) U.S. Cl.
CPC .............. *C12P 5/02* (2013.01); *C12N 9/0077* (2013.01); *C12N 9/0095* (2013.01); *C12N 15/81* (2013.01)

(58) Field of Classification Search
None
See application file for complete search history.

(56) References Cited

U.S. PATENT DOCUMENTS

| 7,238,482 B2 * | 7/2007 | Picataggio | C12P 7/6427 435/134 |
| 2009/0004715 A1 | 1/2009 | Trimbur et al. | |
| 2009/0215140 A1 | 8/2009 | Kurano et al. | |
| 2010/0249470 A1 | 9/2010 | Schirmer et al. | |
| 2011/0117618 A1 * | 5/2011 | Reppas et al. | 435/167 |
| 2011/0124071 A1 * | 5/2011 | Schirmer et al. | 435/167 |

FOREIGN PATENT DOCUMENTS

| JP | 2007-74959 A | 3/2007 | |
| JP | 2007-209213 A | 8/2007 | |
| JP | 2010-528627 A | 8/2010 | |
| JP | 2011-522525 A | 8/2011 | |
| WO | 2006/109588 A1 | 10/2006 | |
| WO | 2009/140695 A1 | 11/2009 | |
| WO | WO-2011103300 A2 * | 8/2011 | ........... C07K 14/395 |

OTHER PUBLICATIONS

James R. Reed et al., "Unusual mechanism of hydrocarbon formation in the housefly: Cytochrome P450 converts aldehyde to the sex pheromone component (Z)-9-tricosene and $CO_2$", Proc. Natl. Acad. Sci. USA, Oct. 1994, pp. 10000-10004, vol. 91.

P. Metzger et al., "*Botryococcus braunii*: a rich source for hydrocarbons and related ether lipids", Appl Microbiol Biotechnol 2005, pp. 486-496, vol. 66.

Andreas Schirmer et al., "Microbial Biosynthesis of Alkanes", Science, Jul. 30, 2010, pp. 559-562, vol. 329.

* cited by examiner

*Primary Examiner* — Paul J Holland
(74) *Attorney, Agent, or Firm* — Sughrue Mion, PLLC

(57) ABSTRACT

A method for producing alkane and a recombinant microorganism with good alkane productivity in a reaction system for synthesizing alkane by alkane synthase activity are provided. Alkane productivity is significantly improved in a system for synthesizing alkane by alkane synthase in the presence of ferredoxin. Specifically, the method for producing alkane according to the present invention comprises synthesizing alkane by alkane synthase in the presence of ferredoxin.

4 Claims, 10 Drawing Sheets
Specification includes a Sequence Listing.

SEQUENCE LISTING

```
<160> NUMBER OF SEQ ID NOS: 28

<210> SEQ ID NO 1
<211> LENGTH: 519
<212> TYPE: DNA
<213> ORGANISM: Saccharomyces cerevisiae
<220> FEATURE:
<221> NAME/KEY: CDS
<222> LOCATION: (1)..(519)

<400> SEQUENCE: 1 atg ctg aaa att gtt act cgg gct gga cac aca gct aga ata tcg aac        48
Met Leu Lys Ile Val Thr Arg Ala Gly His Thr Ala Arg Ile Ser Asn
1               5                   10                  15 atc gca gca cat ctt tta cgc acc tct cca tct ctg ctc aca cgc acc        96
Ile Ala Ala His Leu Leu Arg Thr Ser Pro Ser Leu Leu Thr Arg Thr
                20                  25                  30 acc aca acc aca aga ttt ctg ccc ttc tct acg tct tcg ttc tta aac       144
Thr Thr Thr Thr Arg Phe Leu Pro Phe Ser Thr Ser Ser Phe Leu Asn
            35                  40                  45
```

```
cat ggc cat ttg aaa aaa ccg aaa cca ggc gaa gaa ctg aag ata act      192
His Gly His Leu Lys Lys Pro Lys Pro Gly Glu Glu Leu Lys Ile Thr
         50                  55                  60 ttt att ctg aag gat ggc tcc cag aag acg tac gaa gtc tgt gag ggc      240
Phe Ile Leu Lys Asp Gly Ser Gln Lys Thr Tyr Glu Val Cys Glu Gly
 65                  70                  75                  80 gaa acc atc ctg gac atc gct caa ggt cac aac ctg gac atg gag ggc      288
Glu Thr Ile Leu Asp Ile Ala Gln Gly His Asn Leu Asp Met Glu Gly
                 85                  90                  95 gca tgc ggc ggt tct tgt gcc tgc tcc acc tgt cac gtc atc gtt gat      336
Ala Cys Gly Gly Ser Cys Ala Cys Ser Thr Cys His Val Ile Val Asp
             100                 105                 110 cca gac tac tac gat gcc ctg ccg gaa cct gaa gat gat gaa aac gat      384
Pro Asp Tyr Tyr Asp Ala Leu Pro Glu Pro Glu Asp Asp Glu Asn Asp
         115                 120                 125 atg ctc gat ctt gct tac ggg cta aca gag aca agc agg ctt ggg tgc      432
Met Leu Asp Leu Ala Tyr Gly Leu Thr Glu Thr Ser Arg Leu Gly Cys
130                 135                 140 cag att aag atg tca aaa gat atc gat ggg att aga gtc gct ctg ccc      480
Gln Ile Lys Met Ser Lys Asp Ile Asp Gly Ile Arg Val Ala Leu Pro
145                 150                 155                 160 cag atg aca aga aac gtt aat aac aac gat ttt agt taa                  519
Gln Met Thr Arg Asn Val Asn Asn Asn Asp Phe Ser
                165                 170

<210> SEQ ID NO 2
<211> LENGTH: 172
<212> TYPE: PRT
<213> ORGANISM: Saccharomyces cerevisiae

<400> SEQUENCE: 2

Met Leu Lys Ile Val Thr Arg Ala Gly His Thr Ala Arg Ile Ser Asn
  1               5                  10                  15

Ile Ala Ala His Leu Leu Arg Thr Ser Pro Ser Leu Leu Thr Arg Thr
                 20                  25                  30

Thr Thr Thr Thr Arg Phe Leu Pro Phe Ser Thr Ser Ser Phe Leu Asn
             35                  40                  45

His Gly His Leu Lys Lys Pro Lys Pro Gly Glu Glu Leu Lys Ile Thr
         50                  55                  60

Phe Ile Leu Lys Asp Gly Ser Gln Lys Thr Tyr Glu Val Cys Glu Gly
 65                  70                  75                  80

Glu Thr Ile Leu Asp Ile Ala Gln Gly His Asn Leu Asp Met Glu Gly
                 85                  90                  95

Ala Cys Gly Gly Ser Cys Ala Cys Ser Thr Cys His Val Ile Val Asp
             100                 105                 110

Pro Asp Tyr Tyr Asp Ala Leu Pro Glu Pro Glu Asp Asp Glu Asn Asp
         115                 120                 125

Met Leu Asp Leu Ala Tyr Gly Leu Thr Glu Thr Ser Arg Leu Gly Cys
130                 135                 140

Gln Ile Lys Met Ser Lys Asp Ile Asp Gly Ile Arg Val Ala Leu Pro
145                 150                 155                 160

Gln Met Thr Arg Asn Val Asn Asn Asn Asp Phe Ser
                165                 170

<210> SEQ ID NO 3
<211> LENGTH: 1482
<212> TYPE: DNA
<213> ORGANISM: Saccharomyces cerevisiae
```

<220> FEATURE:
<221> NAME/KEY: CDS
<222> LOCATION: (1)..(1482)

<400> SEQUENCE: 3

```
atg agc ttt gtt caa ata agg cac att tct tca caa ata aac cgt aag      48
Met Ser Phe Val Gln Ile Arg His Ile Ser Ser Gln Ile Asn Arg Lys
1               5                   10                  15 act gta tcc att gtt gga tcg ggg cct tcc ggc ttt tat aca gcg tac      96
Thr Val Ser Ile Val Gly Ser Gly Pro Ser Gly Phe Tyr Thr Ala Tyr
                20                  25                  30 cat tta ctc aag aag tca ccg att cca tta aat gtt act ata tgg gaa     144
His Leu Leu Lys Lys Ser Pro Ile Pro Leu Asn Val Thr Ile Trp Glu
            35                  40                  45 aag tta cct gtt cct ttt ggt tta agt aga tat ggt gtg gca cct gat     192
Lys Leu Pro Val Pro Phe Gly Leu Ser Arg Tyr Gly Val Ala Pro Asp
        50                  55                  60 cat cca gaa gtc aaa aat tgt gaa gaa acg ttt acc aca tgt gca gaa     240
His Pro Glu Val Lys Asn Cys Glu Glu Thr Phe Thr Thr Cys Ala Glu
65                  70                  75                  80 gag ttt tct tcc cct aca aac caa aag cat aaa ttt tcc ttt gtt ggt     288
Glu Phe Ser Ser Pro Thr Asn Gln Lys His Lys Phe Ser Phe Val Gly
                85                  90                  95 ggt ata acc att gga aaa gaa ata ttg ttg aag gaa ttg ctg gat aat     336
Gly Ile Thr Ile Gly Lys Glu Ile Leu Leu Lys Glu Leu Leu Asp Asn
                100                 105                 110 caa gat gct gtt att tta agt tat ggt tgt aca ggg gac aga aag ctg     384
Gln Asp Ala Val Ile Leu Ser Tyr Gly Cys Thr Gly Asp Arg Lys Leu
            115                 120                 125 aat atc cct ggc gaa ctc gga aca aaa ggg gtg ttt agc agt aga gaa     432
Asn Ile Pro Gly Glu Leu Gly Thr Lys Gly Val Phe Ser Ser Arg Glu
        130                 135                 140 ttt gtc aat tgg tac aat ggt cat cct gat ttc gca aag gat aag cga     480
Phe Val Asn Trp Tyr Asn Gly His Pro Asp Phe Ala Lys Asp Lys Arg
145                 150                 155                 160 ttt acc gat ttt gac tgg agc aaa gtt tcg aaa gtt ggt att ata gga     528
Phe Thr Asp Phe Asp Trp Ser Lys Val Ser Lys Val Gly Ile Ile Gly
                165                 170                 175 aac ggt aac gtt gct ctt gat att acg cgt gta ctt att tct aat caa     576
Asn Gly Asn Val Ala Leu Asp Ile Thr Arg Val Leu Ile Ser Asn Gln
                180                 185                 190 att gat gaa ata tgg gaa aat acg gac atc tca tct ctt gca cta aat     624
Ile Asp Glu Ile Trp Glu Asn Thr Asp Ile Ser Ser Leu Ala Leu Asn
            195                 200                 205 ttg cta aga agg gca cct gta aag gac gtt aag cta att gca cga agg     672
Leu Leu Arg Arg Ala Pro Val Lys Asp Val Lys Leu Ile Ala Arg Arg
        210                 215                 220 gat ttc gtt cat tcc aaa ttc acc aac aaa gaa tta aga gaa cta tgg     720
Asp Phe Val His Ser Lys Phe Thr Asn Lys Glu Leu Arg Glu Leu Trp
225                 230                 235                 240 gag tta gaa aag tat ggc ata cgt ggc cgt att gat cct aaa ttt ttc     768
Glu Leu Glu Lys Tyr Gly Ile Arg Gly Arg Ile Asp Pro Lys Phe Phe
                245                 250                 255 cag aaa gaa atg ttt gac cca tct aag tac gat cgt gca ttc aat aga     816
Gln Lys Glu Met Phe Asp Pro Ser Lys Tyr Asp Arg Ala Phe Asn Arg
                260                 265                 270 cga gta gag atg tgt agt gag tat ctc aag cca ttt aat gaa cgt tcg     864
Arg Val Glu Met Cys Ser Glu Tyr Leu Lys Pro Phe Asn Glu Arg Ser
            275                 280                 285 aag aaa aac tat aaa aag gct cct cct cca agc agc gga tat gac aaa     912
```

-continued

```
                    Lys Lys Asn Tyr Lys Lys Ala Pro Pro Ser Ser Gly Tyr Asp Lys
                        290                 295                 300 ttc tgg gag tta gat tat ttg aag act ccc ttg aaa att aat aga gac      960
Phe Trp Glu Leu Asp Tyr Leu Lys Thr Pro Leu Lys Ile Asn Arg Asp
305                 310                 315                 320 gat ttt ggt gca atc aac tct ttg agt tta tgt aac aat cga tta aat     1008
Asp Phe Gly Ala Ile Asn Ser Leu Ser Leu Cys Asn Asn Arg Leu Asn
            325                 330                 335 gaa gat aac agt ttg caa ccc ttg aag gac gtc aat aat att atg aca     1056
Glu Asp Asn Ser Leu Gln Pro Leu Lys Asp Val Asn Asn Ile Met Thr
        340                 345                 350 tat aaa gtg gat ttg ctg att act tca ttg gga tat gca ggc gtt ccc     1104
Tyr Lys Val Asp Leu Leu Ile Thr Ser Leu Gly Tyr Ala Gly Val Pro
    355                 360                 365 atg cct gaa ttc tct aag ttg tct att gga ttt gac aaa gat cat ata     1152
Met Pro Glu Phe Ser Lys Leu Ser Ile Gly Phe Asp Lys Asp His Ile
370                 375                 380 gct aat aaa cag ggt cgt gtt tta act tcc agc gga gaa ata ttc cca     1200
Ala Asn Lys Gln Gly Arg Val Leu Thr Ser Ser Gly Glu Ile Phe Pro
385                 390                 395                 400 cat tta tat gca tct ggt tgg atc cgt aag ggc agc cag ggc gtt att     1248
His Leu Tyr Ala Ser Gly Trp Ile Arg Lys Gly Ser Gln Gly Val Ile
            405                 410                 415 gcc tcg aca atg caa gat gct ttt gaa gtt gga gac aga gta ata caa     1296
Ala Ser Thr Met Gln Asp Ala Phe Glu Val Gly Asp Arg Val Ile Gln
        420                 425                 430 gac ttg gtg gtc agc gga gcg cta tcc tta gag aat tct atc gac ctc     1344
Asp Leu Val Val Ser Gly Ala Leu Ser Leu Glu Asn Ser Ile Asp Leu
    435                 440                 445 tct aat atc aag cac acc aca tgg aag gat tgg gaa aga atc aac aag     1392
Ser Asn Ile Lys His Thr Thr Trp Lys Asp Trp Glu Arg Ile Asn Lys
450                 455                 460 aag gaa ttg ctt cgg ggc aaa aag gaa cac aaa act cgg tca aag ttt     1440
Lys Glu Leu Leu Arg Gly Lys Lys Glu His Lys Thr Arg Ser Lys Phe
465                 470                 475                 480 tta act ttt gaa gag ttg tgg aac ggt gta gaa ggc ata taa             1482
Leu Thr Phe Glu Glu Leu Trp Asn Gly Val Glu Gly Ile
                485                 490

<210> SEQ ID NO 4
<211> LENGTH: 493
<212> TYPE: PRT
<213> ORGANISM: Saccharomyces cerevisiae

<400> SEQUENCE: 4

Met Ser Phe Val Gln Ile Arg His Ile Ser Ser Gln Ile Asn Arg Lys
1               5                   10                  15

Thr Val Ser Ile Val Gly Ser Gly Pro Ser Gly Phe Tyr Thr Ala Tyr
                20                  25                  30

His Leu Leu Lys Lys Ser Pro Ile Pro Leu Asn Val Thr Ile Trp Glu
            35                  40                  45

Lys Leu Pro Val Pro Phe Gly Leu Ser Arg Tyr Gly Val Ala Pro Asp
        50                  55                  60

His Pro Glu Val Lys Asn Cys Glu Glu Thr Phe Thr Cys Ala Glu
65                  70                  75                  80

Glu Phe Ser Ser Pro Thr Asn Gln Lys His Lys Phe Ser Phe Val Gly
                85                  90                  95

Gly Ile Thr Ile Gly Lys Glu Ile Leu Leu Lys Glu Leu Leu Asp Asn
            100                 105                 110
```

```
Gln Asp Ala Val Ile Leu Ser Tyr Gly Cys Thr Gly Asp Arg Lys Leu
        115                 120                 125

Asn Ile Pro Gly Glu Leu Gly Thr Lys Gly Val Phe Ser Ser Arg Glu
130                 135                 140

Phe Val Asn Trp Tyr Asn Gly His Pro Asp Phe Ala Lys Asp Lys Arg
145                 150                 155                 160

Phe Thr Asp Phe Asp Trp Ser Lys Val Ser Lys Val Gly Ile Ile Gly
                165                 170                 175

Asn Gly Asn Val Ala Leu Asp Ile Thr Arg Val Leu Ile Ser Asn Gln
                180                 185                 190

Ile Asp Glu Ile Trp Glu Asn Thr Asp Ile Ser Ser Leu Ala Leu Asn
        195                 200                 205

Leu Leu Arg Arg Ala Pro Val Lys Asp Val Lys Leu Ile Ala Arg Arg
210                 215                 220

Asp Phe Val His Ser Lys Phe Thr Asn Lys Glu Leu Arg Glu Leu Trp
225                 230                 235                 240

Glu Leu Glu Lys Tyr Gly Ile Arg Gly Arg Ile Asp Pro Lys Phe Phe
                245                 250                 255

Gln Lys Glu Met Phe Asp Pro Ser Lys Tyr Asp Arg Ala Phe Asn Arg
                260                 265                 270

Arg Val Glu Met Cys Ser Glu Tyr Leu Lys Pro Phe Asn Glu Arg Ser
        275                 280                 285

Lys Lys Asn Tyr Lys Lys Ala Pro Pro Ser Ser Gly Tyr Asp Lys
290                 295                 300

Phe Trp Glu Leu Asp Tyr Leu Lys Thr Pro Leu Lys Ile Asn Arg Asp
305                 310                 315                 320

Asp Phe Gly Ala Ile Asn Ser Leu Ser Leu Cys Asn Asn Arg Leu Asn
                325                 330                 335

Glu Asp Asn Ser Leu Gln Pro Leu Lys Asp Val Asn Asn Ile Met Thr
                340                 345                 350

Tyr Lys Val Asp Leu Leu Ile Thr Ser Leu Gly Tyr Ala Gly Val Pro
        355                 360                 365

Met Pro Glu Phe Ser Lys Leu Ser Ile Gly Phe Asp Lys Asp His Ile
370                 375                 380

Ala Asn Lys Gln Gly Arg Val Leu Thr Ser Ser Gly Glu Ile Phe Pro
385                 390                 395                 400

His Leu Tyr Ala Ser Gly Trp Ile Arg Lys Gly Ser Gln Gly Val Ile
                405                 410                 415

Ala Ser Thr Met Gln Asp Ala Phe Glu Val Gly Asp Arg Val Ile Gln
                420                 425                 430

Asp Leu Val Val Ser Gly Ala Leu Ser Leu Glu Asn Ser Ile Asp Leu
        435                 440                 445

Ser Asn Ile Lys His Thr Thr Trp Lys Asp Trp Glu Arg Ile Asn Lys
450                 455                 460

Lys Glu Leu Leu Arg Gly Lys Lys Glu His Lys Thr Arg Ser Lys Phe
465                 470                 475                 480

Leu Thr Phe Glu Glu Leu Trp Asn Gly Val Glu Gly Ile
                485                 490

<210> SEQ ID NO 5
<211> LENGTH: 33
<212> TYPE: DNA
<213> ORGANISM: Artificial Sequence
<220> FEATURE:
```

<223> OTHER INFORMATION: Synthetic DNA

<400> SEQUENCE: 5
cacggaattc cagttcgagt ttatcattat caa                                    33

<210> SEQ ID NO 6
<211> LENGTH: 35
<212> TYPE: DNA
<213> ORGANISM: Artificial Sequence
<220> FEATURE:
<223> OTHER INFORMATION: Synthetic DNA

<400> SEQUENCE: 6
ctctggatcc tttgtttgtt tatgtgtgtt tattc                                  35

<210> SEQ ID NO 7
<211> LENGTH: 681
<212> TYPE: DNA
<213> ORGANISM: Saccharomyces cerevisiae

<400> SEQUENCE: 7
ccagttcgag tttatcatta tcaatactgc catttcaaag gatacgtaaa taattaatag       60
tagtgatttt cctaactttta tttagtcaaa aaattagcct tttaattctg ctgtaacccg     120
tacatgccca aaatagggggg cgggttacac agagtatata acatcgtagg tgtctgggtg     180
aacagtttat tcctggcatc cactaaatat aatggagccc gctttttaag ctggcatcca     240
gaaaaaaaaa gaatcccagc accaaaatat tgtttctttc accaaccatc agttcatagg     300
tccattctct tagcgcaact acagagaaca ggggcacaaa caggcaaaaa acgggcacaa     360
cctcaatgga gtgatgcaac ctgcctggag taaatgatga cacaaggcaa ttgacccacg     420
catgtatcta tctcattttc ttacaccttc tattaccttc tgctctctct gatttggaaa     480
aagctgaaaa aaaaggttga aaccagttcc ctgaaattat tcccctactt gactaataag     540
tatataaga cggtaggtat tgattgtaat tctgtaaatc tatttcttaa acttcttaaa     600
ttctactttt atagttagtc tttttttttag ttttaaaaca ccaagaactt agtttcgaat     660
aaacacacat aaacaaacaa a                                                681

<210> SEQ ID NO 8
<211> LENGTH: 32
<212> TYPE: DNA
<213> ORGANISM: Artificial Sequence
<220> FEATURE:
<223> OTHER INFORMATION: Synthetic DNA

<400> SEQUENCE: 8
taggcaattg caagaattac tcgtgagtaa gg                                     32

<210> SEQ ID NO 9
<211> LENGTH: 36
<212> TYPE: DNA
<213> ORGANISM: Artificial Sequence
<220> FEATURE:
<223> OTHER INFORMATION: Synthetic DNA

<400> SEQUENCE: 9
ataagaattc tgtttttatat tgttgtaaa aagtag                                 36

<210> SEQ ID NO 10
<211> LENGTH: 712
<212> TYPE: DNA
<213> ORGANISM: Saccharomyces cerevisiae

<400> SEQUENCE: 10

```
tgttttatat ttgttgtaaa aagtagataa ttacttcctt gatgatctgt aaaaaagaga      60
aaaagaaagc atctaagaac ttgaaaaact acgaattaga aaagaccaaa tatgtatttc     120
ttgcattgac caatttatgc aagttttatat atatgtaaat gtaagtttca cgaggttcta    180
ctaaactaaa ccaccccctt ggttagaaga aaagagtgtg tgagaacagg ctgttgttgt     240
cacacgattc ggacaattct gtttgaaaga gagagagtaa cagtacgatc gaacgaactt     300
tgctctggag atcacagtgg gcatcatagc atgtggtact aaaccctttc cgccattcc      360 agaaccttcg attgcttgtt acaaaacctg tgagccgtcg ctaggacctt gttgtgtgac     420
gaaattggaa gctgcaatca ataggaagac aggaagtcga gcgtgtctgg gttttttcag    480
ttttgttctt tttgcaaaca aatcacgagc gacggtaatt tctttctcga taagaggcca    540
cgtgctttat gagggtaaca tcaattcaag aaggagggaa acacttcctt tttctggccc    600
tgataatagt atgagggtga agccaaaata aaggattcgc gcccaaatcg gcatctttaa    660
atgcaggtat gcgatagttc ctcactcttt ccttactcac gagtaattct tg            712
```

<210> SEQ ID NO 11
<211> LENGTH: 39
<212> TYPE: DNA
<213> ORGANISM: Artificial Sequence
<220> FEATURE:
<223> OTHER INFORMATION: Synthetic DNA

<400> SEQUENCE: 11

```
gagaggatcc aaaaatgcag caggttgcag ccgatttag                             39
```

<210> SEQ ID NO 12
<211> LENGTH: 33
<212> TYPE: DNA
<213> ORGANISM: Artificial Sequence
<220> FEATURE:
<223> OTHER INFORMATION: Synthetic DNA

<400> SEQUENCE: 12

```
cagactcgag ttaagctgct gtaagtccgt agg                                   33
```

<210> SEQ ID NO 13
<211> LENGTH: 696
<212> TYPE: DNA
<213> ORGANISM: Nostoc sp. ATCC27347
<220> FEATURE:
<221> NAME/KEY: CDS
<222> LOCATION: (1)..(696)

<400> SEQUENCE: 13

```
atg cag cag gtt gca gcc gat tta gaa att gat ttc aag agc gaa aaa      48
Met Gln Gln Val Ala Ala Asp Leu Glu Ile Asp Phe Lys Ser Glu Lys
1               5                   10                  15 tat aaa gat gcc tat agt cgc ata aat gcg atc gtg att gaa ggg gaa      96
Tyr Lys Asp Ala Tyr Ser Arg Ile Asn Ala Ile Val Ile Glu Gly Glu
                20                  25                  30 caa gaa gca tac gag aat tac att caa cta tcc caa ctg ctg cca gac     144
Gln Glu Ala Tyr Glu Asn Tyr Ile Gln Leu Ser Gln Leu Leu Pro Asp
            35                  40                  45 gat aaa gaa gac cta att cgc ctc tcg aaa atg gaa agc cgt cac aaa     192
Asp Lys Glu Asp Leu Ile Arg Leu Ser Lys Met Glu Ser Arg His Lys
        50                  55                  60 aaa gga ttt gaa gct tgt gga cgg aac cta caa gta tca cca gat atg     240
```

-continued

```
Lys Gly Phe Glu Ala Cys Gly Arg Asn Leu Gln Val Ser Pro Asp Met
 65                  70                  75                  80 gag ttt gcc aaa gaa ttc ttt gct gga cta cac ggt aac ttc caa aaa      288
Glu Phe Ala Lys Glu Phe Phe Ala Gly Leu His Gly Asn Phe Gln Lys
                 85                  90                  95 gcg gcg gct gaa ggt aaa atc gtt acc tgt cta ttg att cag tcc ctg      336
Ala Ala Ala Glu Gly Lys Ile Val Thr Cys Leu Leu Ile Gln Ser Leu
            100                 105                 110 att att gaa tgt ttt gcg atc gcc gca tac aat atc tac att ccc gtt      384
Ile Ile Glu Cys Phe Ala Ile Ala Ala Tyr Asn Ile Tyr Ile Pro Val
        115                 120                 125 gct gac gat ttt gct cgt aaa atc act gag ggt gta gtc aaa gat gaa      432
Ala Asp Asp Phe Ala Arg Lys Ile Thr Glu Gly Val Val Lys Asp Glu
    130                 135                 140 tac agc cac ctc aac ttc ggc gaa gtt tgg tta cag aaa aat ttt gcc      480
Tyr Ser His Leu Asn Phe Gly Glu Val Trp Leu Gln Lys Asn Phe Ala
145                 150                 155                 160 caa tcc aaa gca gaa tta gaa gaa gct aat cgt cat aat ctt ccc ata      528
Gln Ser Lys Ala Glu Leu Glu Glu Ala Asn Arg His Asn Leu Pro Ile
                165                 170                 175 gtt tgg aaa atg ctc aat caa gtc gcg gat gat gcc gca gtc tta gct      576
Val Trp Lys Met Leu Asn Gln Val Ala Asp Asp Ala Ala Val Leu Ala
            180                 185                 190 atg gaa aaa gaa gcc cta gtc gaa gat ttt atg att cag tac ggc gaa      624
Met Glu Lys Glu Ala Leu Val Glu Asp Phe Met Ile Gln Tyr Gly Glu
        195                 200                 205 gcg tta agt aat att ggc ttc aca acc aga gat att atg cgg atg tca      672
Ala Leu Ser Asn Ile Gly Phe Thr Thr Arg Asp Ile Met Arg Met Ser
    210                 215                 220 gcc tac gga ctt aca gca gct taa                                      696
Ala Tyr Gly Leu Thr Ala Ala
225                 230

<210> SEQ ID NO 14
<211> LENGTH: 231
<212> TYPE: PRT
<213> ORGANISM: Nostoc sp. ATCC27347

<400> SEQUENCE: 14

Met Gln Gln Val Ala Ala Asp Leu Glu Ile Asp Phe Lys Ser Glu Lys
  1               5                  10                  15

Tyr Lys Asp Ala Tyr Ser Arg Ile Asn Ala Ile Val Ile Glu Gly Glu
             20                  25                  30

Gln Glu Ala Tyr Glu Asn Tyr Ile Gln Leu Ser Gln Leu Leu Pro Asp
         35                  40                  45

Asp Lys Glu Asp Leu Ile Arg Leu Ser Lys Met Glu Ser Arg His Lys
     50                  55                  60

Lys Gly Phe Glu Ala Cys Gly Arg Asn Leu Gln Val Ser Pro Asp Met
 65                  70                  75                  80

Glu Phe Ala Lys Glu Phe Phe Ala Gly Leu His Gly Asn Phe Gln Lys
                 85                  90                  95

Ala Ala Ala Glu Gly Lys Ile Val Thr Cys Leu Leu Ile Gln Ser Leu
            100                 105                 110

Ile Ile Glu Cys Phe Ala Ile Ala Ala Tyr Asn Ile Tyr Ile Pro Val
        115                 120                 125

Ala Asp Asp Phe Ala Arg Lys Ile Thr Glu Gly Val Val Lys Asp Glu
    130                 135                 140

Tyr Ser His Leu Asn Phe Gly Glu Val Trp Leu Gln Lys Asn Phe Ala
```

```
                145                 150                 155                 160
Gln Ser Lys Ala Glu Leu Glu Glu Ala Asn Arg His Asn Leu Pro Ile
                165                 170                 175

Val Trp Lys Met Leu Asn Gln Val Ala Asp Asp Ala Val Leu Ala
            180                 185                 190

Met Glu Lys Glu Ala Leu Val Glu Asp Phe Met Ile Gln Tyr Gly Glu
        195                 200                 205

Ala Leu Ser Asn Ile Gly Phe Thr Thr Arg Asp Ile Met Arg Met Ser
    210                 215                 220

Ala Tyr Gly Leu Thr Ala Ala
225                 230

<210> SEQ ID NO 15
<211> LENGTH: 36
<212> TYPE: DNA
<213> ORGANISM: Artificial Sequence
<220> FEATURE:
<223> OTHER INFORMATION: Synthetic DNA

<400> SEQUENCE: 15
cacaggatcc aaaaatgctg aaaattgtta ctcggg                             36

<210> SEQ ID NO 16
<211> LENGTH: 35
<212> TYPE: DNA
<213> ORGANISM: Artificial Sequence
<220> FEATURE:
<223> OTHER INFORMATION: Synthetic DNA

<400> SEQUENCE: 16
ggaactcgag ttaactaaaa tcgttgttat taacg                              35

<210> SEQ ID NO 17
<211> LENGTH: 40
<212> TYPE: DNA
<213> ORGANISM: Artificial Sequence
<220> FEATURE:
<223> OTHER INFORMATION: Synthetic DNA

<400> SEQUENCE: 17
atatgcggcc gcaaaaatga gctttgttca aataaggcac                         40

<210> SEQ ID NO 18
<211> LENGTH: 33
<212> TYPE: DNA
<213> ORGANISM: Artificial Sequence
<220> FEATURE:
<223> OTHER INFORMATION: Synthetic DNA

<400> SEQUENCE: 18
ggccactagt ttatatgcct tctacaccgt tcc                                33

<210> SEQ ID NO 19
<211> LENGTH: 31
<212> TYPE: DNA
<213> ORGANISM: Artificial Sequence
<220> FEATURE:
<223> OTHER INFORMATION: Synthetic DNA

<400> SEQUENCE: 19
gcgcgcggta ccatgcagca ggttgcagcc g                                  31

<210> SEQ ID NO 20
```

<210> SEQ ID NO 20
<211> LENGTH: 34
<212> TYPE: DNA
<213> ORGANISM: Artificial Sequence
<220> FEATURE:
<223> OTHER INFORMATION: Synthetic DNA

<400> SEQUENCE: 20
gcgcgcctcg agttaagctg ctgtaagtcc gtag         34

<210> SEQ ID NO 21
<211> LENGTH: 36
<212> TYPE: DNA
<213> ORGANISM: Artificial Sequence
<220> FEATURE:
<223> OTHER INFORMATION: Synthetic DNA

<400> SEQUENCE: 21
gagatataca tatgccaaag attgttattt tgcctc       36

<210> SEQ ID NO 22
<211> LENGTH: 32
<212> TYPE: DNA
<213> ORGANISM: Artificial Sequence
<220> FEATURE:
<223> OTHER INFORMATION: Synthetic DNA

<400> SEQUENCE: 22
cagactcgag ttaatgctca cgcgcatggt tg           32

<210> SEQ ID NO 23
<211> LENGTH: 336
<212> TYPE: DNA
<213> ORGANISM: Escherichia coli
<220> FEATURE:
<221> NAME/KEY: CDS
<222> LOCATION: (1)..(336)

<400> SEQUENCE: 23

```
atg cca aag att gtt att ttg cct cat cag gat ctc tgc cct gat ggc      48
Met Pro Lys Ile Val Ile Leu Pro His Gln Asp Leu Cys Pro Asp Gly
1               5                   10                  15 gct gtt ctg gaa gct aat agc ggt gaa acc att ctc gac gca gct ctg      96
Ala Val Leu Glu Ala Asn Ser Gly Glu Thr Ile Leu Asp Ala Ala Leu
            20                  25                  30 cgt aac ggt atc gag att gaa cac gcc tgt gaa aaa tcc tgt gct tgc     144
Arg Asn Gly Ile Glu Ile Glu His Ala Cys Glu Lys Ser Cys Ala Cys
        35                  40                  45 acc acc tgc cac tgc atc gtt cgt gaa ggt ttt gac tca ctg ccg gaa     192
Thr Thr Cys His Cys Ile Val Arg Glu Gly Phe Asp Ser Leu Pro Glu
    50                  55                  60 agc tca gag cag gaa gac gac atg ctg gac aaa gcc tgg gga ctg gag     240
Ser Ser Glu Gln Glu Asp Asp Met Leu Asp Lys Ala Trp Gly Leu Glu
65                  70                  75                  80 ccg gaa agc cgt tta agc tgc cag gcg cgc gtt acc gac gaa gat tta     288
Pro Glu Ser Arg Leu Ser Cys Gln Ala Arg Val Thr Asp Glu Asp Leu
                85                  90                  95 gta gtc gaa atc ccg cgt tac act atc aac cat gcg cgt gag cat taa     336
Val Val Glu Ile Pro Arg Tyr Thr Ile Asn His Ala Arg Glu His
            100                 105                 110
```

<210> SEQ ID NO 24
<211> LENGTH: 111
<212> TYPE: PRT
<213> ORGANISM: Escherichia coli

<400> SEQUENCE: 24

Met Pro Lys Ile Val Ile Leu Pro His Gln Asp Leu Cys Pro Asp Gly
1               5                   10                  15

Ala Val Leu Glu Ala Asn Ser Gly Glu Thr Ile Leu Asp Ala Ala Leu
            20                  25                  30

Arg Asn Gly Ile Glu Ile Glu His Ala Cys Glu Lys Ser Cys Ala Cys
        35                  40                  45

Thr Thr Cys His Cys Ile Val Arg Glu Gly Phe Asp Ser Leu Pro Glu
    50                  55                  60

Ser Ser Glu Gln Glu Asp Asp Met Leu Asp Lys Ala Trp Gly Leu Glu
65                  70                  75                  80

Pro Glu Ser Arg Leu Ser Cys Gln Ala Arg Val Thr Asp Glu Asp Leu
                85                  90                  95

Val Val Glu Ile Pro Arg Tyr Thr Ile Asn His Ala Arg Glu His
            100                 105                 110

<210> SEQ ID NO 25
<211> LENGTH: 27
<212> TYPE: DNA
<213> ORGANISM: Artificial Sequence
<220> FEATURE:
<223> OTHER INFORMATION: Synthetic DNA

<400> SEQUENCE: 25
atatccatgg ctgattgggt aacaggc                                           27

<210> SEQ ID NO 26
<211> LENGTH: 32
<212> TYPE: DNA
<213> ORGANISM: Artificial Sequence
<220> FEATURE:
<223> OTHER INFORMATION: Synthetic DNA

<400> SEQUENCE: 26
attcggatcc ttaccagtaa tgctccgctg tc                                     32

<210> SEQ ID NO 27
<211> LENGTH: 747
<212> TYPE: DNA
<213> ORGANISM: Escherichia coli
<220> FEATURE:
<221> NAME/KEY: CDS
<222> LOCATION: (1)..(747)

<400> SEQUENCE: 27 atg gct gat tgg gta aca ggc aaa gtc act aaa gtg cag aac tgg acc        48
Met Ala Asp Trp Val Thr Gly Lys Val Thr Lys Val Gln Asn Trp Thr
1               5                   10                  15 gac gcc ctg ttt agt ctc acc gtt cac gcc ccc gtg ctt ccg ttt acc        96
Asp Ala Leu Phe Ser Leu Thr Val His Ala Pro Val Leu Pro Phe Thr
            20                  25                  30 gcc ggg caa ttt acc aag ctt ggc ctt gaa atc gac ggc gaa cgc gtc       144
Ala Gly Gln Phe Thr Lys Leu Gly Leu Glu Ile Asp Gly Glu Arg Val
        35                  40                  45 cag cgc gcc tac tcc tat gta aac tcg ccc gat aat ccc gat ctg gag       192
Gln Arg Ala Tyr Ser Tyr Val Asn Ser Pro Asp Asn Pro Asp Leu Glu
    50                  55                  60 ttt tac ctg gtc acc gtc ccc gat ggc aaa tta agc cca cga ctg gcg       240
Phe Tyr Leu Val Thr Val Pro Asp Gly Lys Leu Ser Pro Arg Leu Ala
65                  70                  75                  80 gca ctg aaa cca ggc gat gaa gtg cag gtg gtt agc gaa gcg gca gga       288

```
Ala Leu Lys Pro Gly Asp Glu Val Gln Val Val Ser Glu Ala Ala Gly
                85                  90                  95 ttc ttt gtg ctc gat gaa gtg ccg cac tgc gaa acg cta tgg atg ctg      336
Phe Phe Val Leu Asp Glu Val Pro His Cys Glu Thr Leu Trp Met Leu
            100                 105                 110 gca acc ggt aca gcg att ggc cct tat tta tcg att ctg caa cta ggt      384
Ala Thr Gly Thr Ala Ile Gly Pro Tyr Leu Ser Ile Leu Gln Leu Gly
        115                 120                 125 aaa gat tta gat cgc ttc aaa aat ctg gtc ctg gtg cac gcc gca cgt      432
Lys Asp Leu Asp Arg Phe Lys Asn Leu Val Leu Val His Ala Ala Arg
    130                 135                 140 tat gcc gcc gac tta agc tat ttg cca ctg atg cag gaa ctg gaa aaa      480
Tyr Ala Ala Asp Leu Ser Tyr Leu Pro Leu Met Gln Glu Leu Glu Lys
145                 150                 155                 160 cgc tac gaa gga aaa ctg cgc att cag acg gtg gtc agt cgg gaa acg      528
Arg Tyr Glu Gly Lys Leu Arg Ile Gln Thr Val Val Ser Arg Glu Thr
                165                 170                 175 gca gcg ggg tcg ctc acc gga cgg ata ccg gca tta att gaa agt ggg      576
Ala Ala Gly Ser Leu Thr Gly Arg Ile Pro Ala Leu Ile Glu Ser Gly
            180                 185                 190 gaa ctg gaa agc acg att ggc ctg ccg atg aat aaa gaa acc agc cat      624
Glu Leu Glu Ser Thr Ile Gly Leu Pro Met Asn Lys Glu Thr Ser His
        195                 200                 205 gtg atg ctg tgc ggc aat cca cag atg gtg cgc gat aca caa cag ttg      672
Val Met Leu Cys Gly Asn Pro Gln Met Val Arg Asp Thr Gln Gln Leu
    210                 215                 220 ctg aaa gag acc cgg cag atg acg aaa cat tta cgt cgc cga ccg ggc      720
Leu Lys Glu Thr Arg Gln Met Thr Lys His Leu Arg Arg Arg Pro Gly
225                 230                 235                 240 cat atg aca gcg gag cat tac tgg taa                                  747
His Met Thr Ala Glu His Tyr Trp
                245

<210> SEQ ID NO 28
<211> LENGTH: 248
<212> TYPE: PRT
<213> ORGANISM: Escherichia coli

<400> SEQUENCE: 28

Met Ala Asp Trp Val Thr Gly Lys Val Thr Lys Val Gln Asn Trp Thr
1               5                   10                  15

Asp Ala Leu Phe Ser Leu Thr Val His Ala Pro Val Leu Pro Phe Thr
            20                  25                  30

Ala Gly Gln Phe Thr Lys Leu Gly Leu Glu Ile Asp Gly Glu Arg Val
        35                  40                  45

Gln Arg Ala Tyr Ser Tyr Val Asn Ser Pro Asp Asn Pro Asp Leu Glu
    50                  55                  60

Phe Tyr Leu Val Thr Val Pro Asp Gly Lys Leu Ser Pro Arg Leu Ala
65                  70                  75                  80

Ala Leu Lys Pro Gly Asp Glu Val Gln Val Val Ser Glu Ala Ala Gly
                85                  90                  95

Phe Phe Val Leu Asp Glu Val Pro His Cys Glu Thr Leu Trp Met Leu
            100                 105                 110

Ala Thr Gly Thr Ala Ile Gly Pro Tyr Leu Ser Ile Leu Gln Leu Gly
        115                 120                 125

Lys Asp Leu Asp Arg Phe Lys Asn Leu Val Leu Val His Ala Ala Arg
    130                 135                 140

Tyr Ala Ala Asp Leu Ser Tyr Leu Pro Leu Met Gln Glu Leu Glu Lys
```

-continued

```
            145                 150                 155                 160
Arg Tyr Glu Gly Lys Leu Arg Ile Gln Thr Val Val Ser Arg Glu Thr
                165                 170                 175

Ala Ala Gly Ser Leu Thr Gly Arg Ile Pro Ala Leu Ile Glu Ser Gly
                180                 185                 190

Glu Leu Glu Ser Thr Ile Gly Leu Pro Met Asn Lys Glu Thr Ser His
        195                 200                 205

Val Met Leu Cys Gly Asn Pro Gln Met Val Arg Asp Thr Gln Gln Leu
        210                 215                 220

Leu Lys Glu Thr Arg Gln Met Thr Lys His Leu Arg Arg Pro Gly
225                 230                 235                 240

His Met Thr Ala Glu His Tyr Trp
                245
```

METHOD FOR PRODUCING ALKANE AND RECOMBINANT MICROORGANISM CAPABLE OF SYNTHESIZING ALKANE

CROSS REFERENCE TO RELATED APPLICATIONS

This application is a National Stage of International Application No. PCT/JP2011/068522 filed Aug. 15, 2011, the contents of which are incorporated herein by reference in their entirety.

TECHNICAL FIELD

The present invention relates to a method for producing alkane that can be used for a biodiesel fuel, for example, and a recombinant microorganism capable of synthesizing alkane.

BACKGROUND ART

Alkane containing in petroleum is used for various applications after purification via fractional distillation. Furthermore, alkane is not only used widely as a raw material in chemical industry, but also used as a major ingredient of a diesel fuel obtained from petroleum. An example of biotechnology for producing alkane is disclosed in Patent Document 1. Patent Document 1 discloses an attempt of synthesizing alkane with recombinant *Escherichia coli* introduced a blue-green alga-derived alkane synthase gene and an acyl-CoA reductase gene.

Furthermore, Patent Document 2 discloses a microalga (*Pseudochoricystis ellipsoidea*) capable of producing $C_{10-25}$ hydrocarbon. Moreover, Patent Document 3 discloses technology for synthesizing alkane using yeast having fatty acid aldehyde decarbonylase activity to catalyze the conversion of aldehyde into alkane. Furthermore, Non-Patent Document 1 discloses a method for synthesizing alkane from aldehyde using enzyme P450.

Meanwhile, Patent Document 4 discloses a method for biosynthesis of $\alpha,\omega$ alkane diol by culturing recombinant *Escherichia coli* expressing a CYP153-alkane-1-monooxygenase gene, a ferredoxin gene, and a ferredoxin reductase gene in a medium containing alkane or alkane mono-ol.

As described above, whereas recombinant microorganisms expressing alkane synthase genes and microorganisms capable of synthesizing alkane are known, their alkane productivity could not have been sufficient.

PRIOR ART DOCUMENTS

Patent Documents

Patent Document 1: WO2009/140695
Patent Document 2: WO2006/109588
Patent Document 3: JP Patent Publication (Kohyo) No. 2010-528627A
Patent Document 4: JP Patent Publication (Kokai) No. 2007-74959A

Non-Patent Documents

Non-Patent Document 1: Proc. Natl. Acad. Sci. U.S.A. 91, 10000-10004 (1994)

SUMMARY OF THE INVENTION

Problem to be Solved by the Invention

In view of the above circumstances, an object of the present invention is to provide a method for producing alkane and a recombinant microorganism with good alkane productivity in a reaction system for synthesizing alkane by alkane synthase activity.

Means for Solving Problem

As a result of intensive studies to achieve the above object, the present inventors have discovered that alkane productivity is significantly improved in a system for synthesizing alkane by alkane synthase in the presence of ferredoxin. Thus, the present inventors have completed the present invention.

Specifically, the present invention encompasses the following (1) to (14).

(1) A method for producing alkane, comprising synthesizing alkane by alkane synthase in the presence of ferredoxin.
(2) The method for producing alkane according to (1), wherein alkane is synthesized by a microorganism capable of synthesizing alkane.
(3) The method for producing alkane according to (2), wherein the microorganism is a recombinant microorganism into which an alkane synthase gene is introduced.
(4) The method for producing alkane according to (2), wherein the microorganism is a recombinant microorganism into which a ferredoxin gene is introduced.
(5) The method for producing alkane according to (2), wherein the microorganism is a recombinant microorganism into which an alkane synthase gene and a ferredoxin gene are introduced.
(6) The method for producing alkane according to (1), wherein alkane is synthesized in the presence of ferredoxin NADPH reductase in addition to the ferredoxin.
(7) The method for producing alkane according to (6), wherein alkane is synthesized by a microorganism capable of synthesizing alkane into which a ferredoxin NADPH reductase gene is introduced.
(8) The method for producing alkane according to any one of (3) to (5) and (7), wherein the recombinant microorganism is derived from yeast.
(9) The method for producing alkane according to (1), wherein the alkane synthase has activity to convert aldehyde into alkane.
(10) The method for producing alkane according to (1), comprising producing $C_{9-16}$ alkane.
(11) A recombinant microorganism capable of synthesizing alkane, wherein a ferredoxin gene has been introduced.
(12) The recombinant microorganism according to (11), wherein a ferredoxin NADPH reductase gene has further been introduced.
(13) The recombinant microorganism according to (11), wherein the ability to synthesize alkane has been imparted by introduction of the alkane synthase gene.
(14) The recombinant microorganism according to (11), which is recombinant yeast.

Effects of the Invention

According to the present invention, the efficiency of alkane synthesis in a reaction system for synthesizing alkane by alkane synthase, and specifically, alkane productivity, can be improved. Specifically, with the method for producing alkane according to the present invention, alkane can be produced with a very high level of production efficiency. Thus, the method can contribute to lowering alkane production cost. Also, the recombinant microorganism according to the present invention has greater ability to synthesize alkane than conventional microorganisms capable of synthesizing alkane, and thus it is very useful in alkane production.

EMBODIMENTS FOR CARRYING OUT THE INVENTION

Figure 1:
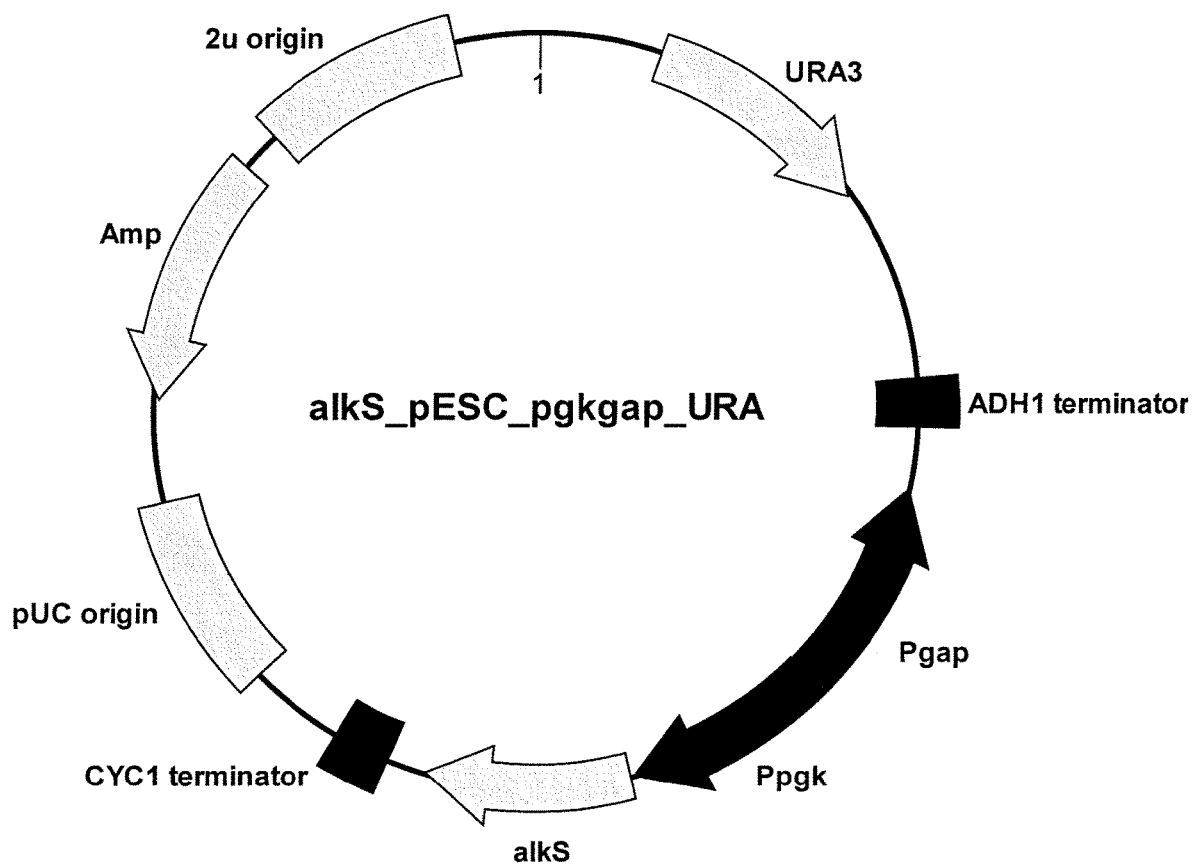
FIG. 1 schematically shows the composition of pESCpg-kgap-URA-alkS.

The present invention is hereafter described in greater detail with reference to drawings and examples.

According to the present invention, ferredoxin is caused to be present in a system for synthesizing alkane by alkane synthase, so as to improve alkane productivity. Here, the term "system for synthesizing alkane by alkane synthase" refers to in vivo systems including microorganisms capable of synthesizing alkane, and recombinant microorganisms with the imparted ability to synthesize alkane, and in vitro systems for synthesizing alkane by alkane synthase in reaction solutions containing substrates. In any of these systems for synthesizing alkane, alkane productivity is more improved in the presence of ferredoxin, compared with that in the absence of ferredoxin.

Moreover, in addition to ferredoxin, ferredoxin NADPH reductase (may also be referred to as "ferredoxin NADP$^+$ reductase") is caused to be present, so as to be able to more significantly improve alkane productivity. Specifically, ferredoxin and ferredoxin NADPH reductase are caused to be present in a system for synthesizing alkane by alkane synthase, so that alkane productivity is more significantly improved compared with cases in which ferredoxin alone is present.

<Ferredoxin>

Ferredoxin is an iron-sulfur protein containing iron-sulfur clusters (Fe—S clusters) therewithin and functioning as an electron carrier. Ferredoxin can be caused to be present in a system for synthesizing alkane by alkane synthase through introduction of a gene encoding ferredoxin into a microorganism capable of synthesizing alkane or a recombinant microorganism with the imparted ability to synthesize alkane, for example. Such a ferredoxin gene is not particularly limited, a ferredoxin gene from any organisms can be used. For example, with reference to a database registered gene information such as DDBJ/EMBL/GenBank International Nucleotide Sequence Database, the nucleotide sequences relating to ferredoxin genes and the amino acid sequences of ferredoxin from various species of organisms can be specified.

Once the nucleotide sequence of a ferredoxin gene can be specified, the gene can be isolated according to a standard method. For example, a predetermined organism-derived ferredoxin gene may be entirely synthesized based on the thus specified nucleotide sequence. Alternatively, primers are designed based on the thus specified nucleotide sequence, and then a ferredoxin gene can also be isolated by PCR using the primers and the genome of a predetermined organism as a template.

In particular, when a ferredoxin gene is introduced into a microorganism capable of synthesizing alkane or a recombinant microorganism having the imparted ability to synthesize alkane, a preferable ferredoxin gene is derived from the relevant microorganism. For example, when recombinant yeast to be used herein has acquired the ability to synthesize alkane as a result of introduction of alkane synthesis-related gene into predetermined yeast, the relevant yeast-derived ferredoxin gene is introduced into cell.

More specifically, *S. cerevisiae*-derived ferredoxin gene is preferably used for recombinant yeast (recombinant *S. cerevisiae*) that has acquired the ability to synthesize alkane. In addition, *S. cerevisiae*-derived ferredoxin gene is known as an YAH1 gene (or Yfdx gene). The nucleotide sequence of the *S. cerevisiae*-derived ferredoxin gene and the amino acid sequence of ferredoxin encoded by the gene are shown in SEQ ID NOS: 1 and 2, respectively.

In addition, an example of a ferredoxin gene is not limited to the gene encoding the amino acid sequence shown in SEQ ID NO: 2, and may also be a gene encoding a protein functioning as ferredoxin and comprising an amino acid sequence that has 70% or more identity, preferably 80% or more identity, more preferably 90% or more identity, further preferably 95% identity, and most preferably 98% or more identity with the amino acid sequence shown in SEQ ID NO: 2. Here, the value of identity refers to a value that can be calculated based on default setting using the BLASTN or BLASTX program equipped with the BLAST algorithm. Specifically, the value of identity is found by calculating the number of amino acid residues that completely match the others when a pairwise alignment analysis is conducted for a pair of amino acid sequences, and then finding the proportion of the number of such residues in all the amino acid residues compared.

Moreover, an example of a ferredoxin gene is not limited to the gene encoding the amino acid sequence shown in SEQ ID NO: 2, and may be a gene encoding a protein that comprises an amino acid sequence having a deletion, a substitution, an addition, or an insertion of 1 to 20 amino acids, preferably 1 to 15 amino acids, more preferably 1 to 10 amino acids, and further preferably 1 to 5 amino acids with respect to the amino acid sequence shown in SEQ ID NO: 2 and functions as ferredoxin.

Furthermore, an example of a ferredoxin gene is not limited to the gene comprising the nucleotide sequence shown in SEQ ID NO: 1, and may be a gene that hybridizes under stringent conditions to all or a part of a complementary strand of DNA comprising the nucleotide sequence shown in SEQ ID NO: 1, and encodes a protein functioning as ferredoxin. Here, the term "stringent conditions" refers to conditions wherein namely a specific hybrid is formed, but any non-specific hybrid is not formed. For example, such conditions can be adequately determined in reference to the Molecular Cloning: A Laboratory Manual (Third Edition). Specifically, stringency can be set based on the temperature and the concentration of salts contained in a solution for southern hybridization, and the temperature and the concentration of salts contained in a solution for a washing step of southern hybridization.

In addition, as a method for preparing DNA comprising: a nucleotide sequence that encodes an amino acid sequence having a deletion, a substitution, an addition, or an insertion of predetermined amino acids with respect to the amino acid sequence shown in SEQ ID NO: 2; or a nucleotide sequence that differs from the nucleotide sequence shown in SEQ ID NO: 1, any conventionally known technique can be adequately used without particular limitation. For example, predetermined nucleotides can be substituted using site-directed mutagenesis. Examples of site-directed mutagenesis include T. Kunkel's site-directed mutagenesis (Kunkel, T. A. Proc. Nati. Acad. Sci. U.S.A. 82, 488-492 (1985)), and the Gapped duplex method. Moreover, mutagenesis can also be carried out using a mutagenesis kit using site-directed mutagenesis (e.g., Mutan-K (Takara Shuzo Co., Ltd.) and Mutan-G (Takara Shuzo Co., Ltd.)), or, a LA PCR in vitro Mutagenesis series kit (Takara Shuzo Co., Ltd.).

Meanwhile, when ferredoxin is caused to be present in an in vitro system for synthesizing alkane by alkane synthase in a reaction solution containing a substrate, ferredoxin that is the product of the above ferredoxin gene is used. Ferredoxin as a protein can be obtained by conventionally known techniques. Ferredoxin that can be used herein may be in an unpurified state, a partially purified state, or a purified state.

<Ferredoxin NADPH Reductase>

Ferredoxin NADPH reductase is an enzyme the catalyzes the oxidation-reduction reaction between ferredoxin and NADPH. Ferredoxin NADPH reductase can be caused to be present together with ferredoxin in a system for synthesizing alkane by alkane synthase through introduction of a gene encoding ferredoxin and a gene encoding ferredoxin NADPH reductase into a microorganism capable of synthesizing alkane or a recombinant microorganism to which the ability to synthesize alkane has been imparted, for example. As a ferredoxin NADPH reductase gene, a gene from any organism can be used without particular limitation. For example, with reference to a database registered gene information, such as the DDBJ/EMBL/GenBank International Nucleotide Sequence Database, nucleotide sequences relating to ferredoxin NADPH reductase genes and the amino acid sequences of ferredoxin NADPH reductases from various biological species can be specified.

Once the nucleotide sequence of a ferredoxin NADPH reductase gene can be specified, the gene can be isolated according to a standard method. For example, a predetermined organism-derived ferredoxin NADPH reductase gene can be entirely synthesized based on the thus specified nucleotide sequence, or primers can be designed based on the thus specified nucleotide sequence, and then the ferredoxin NADPH reductase gene can be isolated by PCR using the genome of the predetermined organism as a template and the primers.

In particular, when a ferredoxin gene and a ferredoxin NADPH reductase gene are introduced into a microorganism capable of synthesizing alkane, or a recombinant microorganism having the imparted ability to synthesize alkane, a preferable ferredoxin NADPH reductase gene is a gene derived from the relevant microorganism. Moreover, a ferredoxin NADPH reductase gene is more preferably a gene derived from the same organism as the one from which a ferredoxin gene to be introduced is derived. For example, when recombinant yeast to be used herein has acquired the ability to synthesize alkane as a result of introduction of an alkane synthesis-related gene into predetermined yeast, the ferredoxin gene and the ferredoxin NADPH reductase gene derived from the relevant yeast are introduced.

More specifically, the S. cerevisiae-derived ferredoxin gene and the S. cerevisiae-derived ferredoxin NADPH reductase gene are preferably used for recombinant yeast (recombinant S. cerevisiae) that has acquired the ability to synthesize alkane. In addition, the S. cerevisiae-derived ferredoxin NADPH reductase gene is known as the ARH1 gene (or the Yfdr gene). The nucleotide sequence of the S. cerevisiae-derived ferredoxin NADPH reductase gene and the amino acid sequence of ferredoxin NADPH reductase encoded by the gene are shown in SEQ ID NOS: 3 and 4, respectively.

In addition, an example of a ferredoxin NADPH reductase gene is not limited to the gene encoding the amino acid sequence shown in SEQ ID NO: 4, and may also be a gene encoding a protein that functions as ferredoxin NADPH reductase and comprises an amino acid sequence having 70% or more identity, preferably 80% or more identity, more preferably 90% or more identity, further preferably 95% identity, and most preferably 98% or more identity with the amino acid sequence shown in SEQ ID NO: 4. Here, the value of identity can be calculated based on default setting using the BLASTN or BLASTX program equipped with the BLAST algorithm. In addition, the value of identity is found by calculating the number of amino acid residues that completely match the others when a pairwise alignment analysis is conducted for a pair of amino acid sequences, and then finding the proportion of the number of such residues in all the amino acid residues compared.

Moreover, an example of a ferredoxin NADPH reductase gene is not limited to the gene encoding the amino acid sequence shown in SEQ ID NO: 4, and may be a gene encoding a protein that comprises an amino acid sequence having a deletion, a substitution, an addition, or an insertion of 1 to 50 amino acids, preferably 1 to 40 amino acids, more preferably 1 to 30 amino acids, and further preferably 1 to 20 amino acids with respect to the amino acid sequence shown in SEQ ID NO: 4 and functions as ferredoxin NADPH reductase.

Furthermore, an example of a ferredoxin NADPH reductase gene is not limited to the gene comprising the nucleotide sequence shown in SEQ ID NO: 3, and may be a gene that hybridizes under stringent conditions to all or a part of a complementary strand of DNA comprising the nucleotide sequence shown in SEQ ID NO: 3, and encodes a protein functioning as ferredoxin NADPH reductase. Here, the term "stringent conditions" refers to conditions wherein namely a specific hybrid is formed, but any non-specific hybrid is not formed. For example, such conditions can be adequately determined in reference to the Molecular Cloning: A Laboratory Manual (Third Edition). Specifically, stringency can be set based on the temperature and the concentration of salts contained in a solution for southern hybridization, and the temperature and the concentration of salts contained in a solution for a washing step of southern hybridization.

In addition, as a method for preparing DNA comprising: a nucleotide sequence that encodes an amino acid sequence having a deletion, a substitution, an addition, or an insertion of predetermined amino acids with respect to the amino acid sequence shown in SEQ ID NO: 4; or a nucleotide sequence that differs from the nucleotide sequence shown in SEQ ID NO: 3, any conventionally known technique can be adequately used without particular limitation. For example, predetermined nucleotides can be substituted using site-directed mutagenesis. Examples of site-directed mutagenesis include T. Kunkel's site-directed mutagenesis (Kunkel, T. A. Proc. Nati. Acad. Sci. U.S.A. 82, 488-492 (1985)), and the Gapped duplex method. Moreover, mutagenesis can also be carried out using a mutagenesis kit using site-directed mutagenesis (e.g., Mutan-K (Takara Shuzo Co., Ltd.) and Mutan-G (Takara Shuzo Co., Ltd.)), or, a LA PCR in vitro Mutagenesis series kit (Takara Shuzo Co., Ltd.).

Meanwhile, when ferredoxin and ferredoxin NADPH reductase are caused to be present in an in vitro system for synthesizing alkane by alkane synthase in a reaction solution containing a substrate, ferredoxin NADPH reductase, which is the product of the above-described ferredoxin NADPH reductase gene, is used. Ferredoxin NADPH reductase as a protein can be obtained by conventionally known techniques. Ferredoxin NADPH reductase that can be used herein may be in an unpurified state, a partially purified state, or a purified state.

<Recombinant Microorganism>

In the present invention, a microorganism into which the above ferredoxin gene and ferredoxin NADPH reductase gene are introduced is a microorganism capable of synthesizing alkane or a recombinant microorganism to which the ability to synthesize alkane has been imparted.

Examples of a microorganism capable of synthesizing alkane include *Synechococcus elongatus* PCC7942, *S. elongatus* PCC6301, *Synechocystis* sp. PCC6803, *Prochlorococcus marinus* CCMP 1986, *Anabaena variabilis* ATCC29413, *Nostoc punctiforme* PCC73102, *Gloeobacter violaceus* PCC7421, *Nostoc* sp. PCC7120, *Cyanothece* sp. PCC7425 and *Cyanothece* sp. ATCC51142 (reference: Science 30 Jul. 2010. Vol. 329, No. 5991, pp. 559-562).

Furthermore, an example of a recombinant microorganism to which the ability to synthesize alkane has been imparted is a recombinant microorganism prepared by introducing an alkane synthase gene isolated from the above microorganism capable of synthesizing alkane. For example, as alkane synthase genes, the alkS gene isolated from *Nostoc* sp. ATCC27347 (PCC7120) and the gene (described in Science 30 Jul. 2010. Vol. 329, No. 5991, pp. 559-562) and WO 2009/140695) can be used. More specifically, for example, alkane synthase genes and the like isolated from *Nostoc punctiforme* PCC73102, *Synechococcus elongates* PCC7942, *Synechocystis* sp. PCC6803, *Cyanothece* sp. ATCC51142, *Acaryochlloris marina* MBIC11017, *Gleobacter violaceus* PCC7421 and *Prochlorococcus marinus* str. MIT9303 can be used.

An example of a microorganism into which an alkane synthase gene is introduced is yeast. Examples of yeast include, but are not particularly limited to, yeast of the genus *Pichia* such as *Pichia stipitis*, yeast of the genus *Saccharomyces* such as *Saccharomyces cerevisiae*, and yeast of the genus *Candida* such as *Candida tropicalis* and *Candida prapsilosis*. Of these examples, as a microorganism into which an alkane synthase gene is introduced, *Saccharomyces cerevisiae* is preferably used. As an example, the *Nostoc* sp. ATCC27347-derived alkS gene is introduced into *Saccharomyces cerevisiae*, and then the resulting recombinant *Saccharomyces cerevisiae* capable of synthesizing alkane is preferably used.

The above ferredoxin gene is introduced into the genome of a microorganism as a host, such as the genome of yeast, so that a recombinant microorganism such as recombinant yeast that can be used in the present invention can be prepared. In addition to the above ferredoxin gene, the above ferredoxin NADPH reductase gene is introduced into the genome of a microorganism as a host, such as the genome of yeast, so that a recombinant microorganism such as recombinant yeast that can be used in the present invention can be prepared.

For example, a DNA fragment containing a ferredoxin gene and a ferredoxin NADPH reductase gene is ligated to an expression vector and preferably a multicopy vector, which functions in a host microorganism, so as to prepare recombinant DNA, and then the recombinant DNA is introduced into the microorganism for transformation. Examples of an expression vector that can be used herein include, but are not particularly limited to, a plasmid vector, and a chromosome transfer vector that can be incorporated into the genome of a host organism. An expression vector to be used herein is not particularly limited, and may be adequately selected from all available expression vectors depending on host microorganisms. In addition, examples of an expression vector include plasmid DNA, bacteriophage DNA, retrotransposon DNA, and artificial chromosome DNA (YAC: yeast artificial chromosome).

Examples of plasmid DNA include YCp-type *Escherichia coli*-yeast shuttle vectors such as pRS413, pRS414, pRS415, pRS416, YCp50, pAUR112, and pAUR123, YEp-type *Escherichia coli*-yeast shuttle vectors such as pYES2 and YEp13, YIp-type *Escherichia coli*-yeast shuttle vectors such as pRS403, pRS404, pRS405, pRS406, pAUR101, and pAUR135, *Escherichia coli*-derived plasmids (ColE-based plasmids such as pBR322, pBR325, pUC18, pUC19, pUC118, pUC119, pTV118N, pTV119N, pBluescript, pHSG298, pHSG396, and pTrc99A, p15A-based plasmids such as pACYC177 and pACYC184, and pSC101-based plasmids such as pMW118, pMW119, pMW218 and pMW219), *Agrobacterium*-derived plasmids (e.g., pBI101), *Bacillus subtilis*-derived plasmids (e.g., pUB110, and pTP5). Examples of phage DNA include λ phage (Charon4A, Charon21A, EMBL3, EMBL4, λgt10, λgt11, and λZAP), φX174, M13mp18 and M13mp19. Examples of retrotransposon include a Ty factor and the like. An example of a YAC vector is pYACC2. Furthermore, animal viruses such as a retrovirus or a vaccinia virus, and insect virus vectors such as a baculovirus can also be used herein.

A ferredoxin gene and a ferredoxin NADPH reductase gene should be incorporated into an expression vector, so that each gene can be expressed. The expression " . . . incorporated . . . so that each gene can be expressed" means that the ferredoxin gene and the ferredoxin NADPH reductase gene are ligated to predetermined promoters and then incorporated into a vector so that the genes are expressed under the control of the promoters in a host organism introduced the gene. In addition to a ferredoxin gene and a ferredoxin NADPH reductase gene, a promoter and a terminator, a cis element if desired such as an enhancer, a splicing signal, a polyA addition signal, a selection marker, a ribosomal binding sequence (SD sequence) and the like can be ligated to an expression vector. In addition, examples of a selection marker include antibiotic resistance genes such as an ampicillin resistance gene, a kanamycin resistance gene, and a hygromycin resistance gene.

Moreover, as a transformation method using an expression vector, a conventionally known method can be adequately employed. Examples of a transformation method include a calcium chloride method, a competent cell method, a protoplast or a spheroplast method, and an electrical pulse method.

Meanwhile, a ferredoxin gene and a ferredoxin NADPH reductase gene can be introduced, so that the number of copies of the genes can be increased. Specifically, a ferredoxin gene and a ferredoxin NADPH reductase gene may be introduced so that the multiple copies thereof are present on the chromosomal DNA of a microorganism. The multiple copies of a ferredoxin gene and a ferredoxin NADPH reductase gene can be introduced into the chromosomal DNA of a microorganism by homologous recombination using a sequence, the multiple copies thereof are present on the chromosomal DNA, as a target.

Furthermore, the expression of a ferredoxin gene and a ferredoxin NADPH reductase gene can be enhanced by various methods, for example, substituting expression regulatory sequences (i.e. promoters) of endogenous or introduced ferredoxin and ferredoxin NADPH reductase genes, those capable of increasing the expression levels of the genes, or introducing a regulator sequence that increases the expression level of a predetermined gene. Examples of such a promoter that enables high-level gene expression include, but are not particularly limited to, a lac promoter, a trp promoter, a trc promoter, and a pL promoter. Furthermore, endogenous or introduced ferredoxin and ferredoxin NADPH reductase genes can be altered so that the genes can be expressed at higher levels by introducing mutations into expression control regions for the genes.

<Alkane Production>

As explained above, according to the present invention, alkane can be synthesized with good productivity in an in vivo system such as a microorganism capable of synthesizing alkane or a recombinant microorganism to which the ability to synthesize alkane has been imparted, or in an in vitro system for synthesizing alkane by alkane synthase in a reaction solution containing a substrate.

With a system using a microorganism capable of synthesizing alkane or a recombinant microorganism to which the ability to synthesize alkane has been imparted, alkane can be produced in a medium suitable for these microorganisms by culturing in the medium. More specifically, according to the present invention, the ability to synthesize alkane by alkane synthase can be improved, and as a result, alkane productivity can be improved.

Here, the expression "the ability to synthesize alkane is improved" means that the activity of alkane synthase to convert aldehyde into alkane is improved. Specifically, the reaction efficiency of a reaction conducted by alkane synthase to synthesize alkane using aldehyde as a substrate is improved because of the presence of ferredoxin. For example, the AlkS protein that is encoded by the alkS gene isolated from the above Nostoc sp. ATCC27347 (PCC7120) exhibits activity to convert tetradecanol into tetradecane. In the presence of ferredoxin, the protein can synthesize tetradecane in a significantly higher amount than that in the absence of ferredoxin. Also, at this time, the presence of ferredoxin NADPH reductase in addition to ferredoxin makes it possible to synthesize even a higher amount of tetradecane.

Similarly, with an in vitro system for synthesizing alkane by alkane synthase in a reaction solution containing a substrate, the reaction efficiency of a reaction conducted by alkane synthase to synthesize alkane using aldehyde as a substrate is improved by the presence of ferredoxin. Therefore, according to the present invention, alkane productivity can also be improved in this reaction system.

In the present invention, an example of alkane to be produced herein is not particularly limited, and include alkane having a carbon number ranging from 9 to 16, and preferably ranging from 13 to 16. These alkane examples are highly viscous liquids, which can be used for light oil (diesel fuel) or aviation fuel. Such alkane is isolated from the above in vivo or in vitro reaction system according to a general method, and then can be purified.

EXAMPLES

Hereafter, the present invention is described in greater detail with reference to the examples, although the technical scope of the present invention is not limited to the following examples.

Example 1

In this example, recombinant yeast was prepared by imparting thereto the ability to produce alkane and introducing a ferredoxin gene and/or a ferredoxin NADPH reductase gene thereinto, following which the effects of ferredoxin and ferredoxin NADPH reductase on alkane productivity were confirmed.

<Construction of pESCpgkgap-HIS>

For the purpose of constitutive expression of cloned genes, constitutive promoters (Ppgk and Pgap) were inserted into a pESC vector (STRATAGENE). Pgap is a Saccharomyces cerevisiae YPH499-derived Glyceraldehyde-3-Phosphate Dehydrogenase (gap) gene promoter. First, a DNA fragment containing Pgap was obtained by PCR using genomic DNA that had been purified from the YPH499 yeast strain using Gen-torukun (Takara Bio Inc.) as a template. Polymerase used herein was KOD-Plus-Ver. 2 (Toyobo Co., Ltd.). For amplification of the DNA fragment containing Pgap, the following pair of primers were designed and the composition of the reaction solution and reaction cycle conditions were as follows.

```
(Primer #1) EcoR I-Pgap-F,
                                       (SEQ ID NO: 5)
5'-CACGGAATTCCAGTTCGAGTTTATCATTATCAA-3'

(Primer #2) BamH I-Pgap-R,
                                       (SEQ ID NO: 6)
5'-CTCTGGATCCTTTGTTTGTTTATGTGTGTTTATTC-3'
```

[Composition of Reaction Solution]

| | |
|---|---|
| YPH499 genomic DNA (100 ng/µl) | 1 µl |
| 10x buffer for KOD-Plus-Ver.2 | 5 µl |
| 2 mM dNTPs | 5 µl |
| 25 mM MgSO$_4$ | 4 µl |
| Primer #1 (10 µM) | 1.5 µl |
| Primer #2 (10 µM) | 1.5 µl |
| KOD-Plus (1 U/µl) | 1 µl |
| dH$_2$O | 31 µl |
| | 50 µl |

[Reaction Cycle Conditions]
95 degrees C. for 2 minutes-(95 degrees C. for 30 seconds, 55 degrees C. for 30 seconds, 72 degrees C. for 2 minutes)× 25 cycles-72 degrees C. for 3 minutes-4 degrees C. stock The PCR product was purified using a MinElute PCR purification kit (QIAGEN), and then digested with BamH I and EcoR I restriction enzymes. After agarose gel electrophoresis, a fragment of 0.7-kbp was excised and then purified using a MinElute Gel extraction kit (QIAGEN). The resultant was ligated to a pESC-HIS vector that had been digested with BamH I and EcoR I restriction enzymes. The thus obtained sequence was sequenced and thus the construction of the target plasmid was confirmed. The nucleotide sequence of Pgap is shown in SEQ ID NO: 7. The thus obtained plasmid was designated pESCgap-HIS.

Next, the *Saccharomyces cerevisiae* YPH499-derived phosphoglycerate kinase (pgk) gene promoter, Ppgk, was obtained as follows. First, a DNA fragment containing Ppgk was obtained by PCR using genomic DNA that had been purified from yeast YPH499 using Gen-torukun (Takara Bio Inc.), as a template. Polymerase used herein was KOD-Plus-Ver.2 (Toyobo Co., Ltd.). For amplification of the DNA fragment containing Ppgk, the following pair of primers were designed and the composition of the reaction solution and reaction cycle conditions were as follows.

```
(Primer #1) Mun I-Ppgk1-F,
                                    (SEQ ID NO: 8)
5'-TAGGCAATTGCAAGAATTACTCGTGAGTAAGG-3'

(Primer #2) EcoR I-Ppgk1-R,
                                    (SEQ ID NO: 9)
5'-ATAAGAATTCTGTTTTATATTTGTTGTAAAAAGTAG-3'
```

[Composition of Reaction Solution]

| | |
|---|---|
| YPH499 genomic DNA (100 ng/μl) | 1 μl |
| 10x buffer for KOD-Plus-Ver.2 | 5 μl |
| 2 mM dNTPs | 5 μl |
| 25 mM MgSO$_4$ | 4 μl |
| Primer #1 (10 μM) | 1.5 μl |
| Primer #2 (10 μM) | 1.5 μl |
| KOD-Plus (1 U/μl) | 1 μl |
| dH$_2$O | 31 μl |
| | 50 μl |

[Reaction Cycle Conditions]
95 degrees C. for 2 minutes-(95 degrees C. for 30 seconds, 55 degrees C. for 30 seconds, 72 degrees C. for 2 minutes)× 25 cycles-72 degrees C. for 3 minutes-4 degrees C. stock The PCR product was purified using a MinElute PCR purification kit (QIAGEN), and then digested with Mun I and EcoR I restriction enzymes. After agarose gel electrophoresis, a 0.7-kbp fragment was excised and then purified using a MinElute Gel extraction kit (QIAGEN). The resultant was digested with the EcoR I restriction enzyme, and then it was ligated to the pESCgap-HIS vector that had been subjected to BAP treatment. It was confirmed by colony PCR that the insert had been ligated into the correct direction, and then a plasmid was constructed. The sequence was sequenced and thus the construction of the target plasmid was confirmed. The nucleotide sequence of Ppgk is shown in SEQ ID NO: 10. The thus obtained plasmid was designated pESCpgkgap-HIS.

<Construction of pESCpgkgap-URA>

The above-constructed pESCpgkgap-HIS was digested with Bam H I and Not I restriction enzymes. The thus obtained 1.4-kbp insert fragment was ligated to a pESC-URA vector that had been digested with Bam H I and Not I restriction enzymes. The thus obtained sequence was sequenced, and then the construction of the target plasmid was confirmed. The thus obtained plasmid was designated pESCpgkgap-URA.

<Construction of Plasmid (pESCpgkgap-URA-alkS) for the Expression of *Nostoc* Sp. ATCC 27347-Derived Alkane Synthase Gene>

A DNA fragment containing an alkane synthase gene (alkS gene) was obtained by PCR using the genomic DNA of *Nostoc* sp. AT27347 as a template. KOD-Plus-Ver.2 (Toyobo Co., Ltd.) was used for PCR. For amplification of the DNA fragment containing the alkS gene, the following pair of primers were designed and the composition of the reaction solution and reaction cycle conditions were as follows.

```
(Primer #1) YalkS_F2,
                                    (SEQ ID NO: 11)
5'-GAGAGGATCCAAAAATGCAGCAGGTTGCAGCCGATTTAG-3'

(Primer #2) YalkS_R2,
                                    (SEQ ID NO: 12)
5'-CAGACTCGAGTTAAGCTGCTGTAAGTCCGTAGG-3'
```

[Composition of Reaction Solution]

| | |
|---|---|
| *Nostoc* sp. PCC27347 genomic DNA (100 ng/μl) | 1 μl |
| 10x buffer for KOD-Plus-Ver.2 | 5 μl |
| 2 mM dNTPs | 5 μl |
| 25 mM MgSO$_4$ | 4 μl |
| Primer #1 (10 μM) | 1.5 μl |
| Primer #2 (10 μM) | 1.5 μl |
| KOD-Plus (1 U/μl) | 1 μl |
| dH$_2$O | 31 μl |
| | 50 μl |

[Reaction Cycle Conditions]
94 degrees C. for 2 minutes-(98 degrees C. for 10 seconds, 55 degrees C. for 30 seconds, 68 degrees C. for 1 minute and 30 seconds)×30 cycles-68 degrees C. for 3 minutes-16 degrees C. stock The PCR product was purified using a QIAquick PCR purification kit (QIAGEN), and then digested with BamH I and Xho I restriction enzymes. After agarose gel electrophoresis, an approximately 0.7-kb fragment was excised, and then purified using a MinElute Gel extraction kit (QIAGEN), thereby obtaining an Insert portion. The pESCpgk-gap-URA plasmid was digested with BamH I and Xho I restriction enzymes. An approximately 7.4-kb fragment was excised, and then purified with a MinElute Gel extraction kit (QIAGEN), thereby obtaining a Vector portion.

The above Insert portion and Vector portion were ligated using a Ligation-Convenience Kit (Nippon Gene Co., Ltd.) to transform *Escherichia coli* HST08 (Takara Bio Inc.). Colonies grown on an LB agar medium containing 50 μg/ml ampicillin were cultured in an LB liquid medium containing 50 μg/ml ampicillin, and thus a plasmid was extracted. A QIAprep spin Miniprep Kit (QIAGEN) was used for extraction. The thus obtained plasmid was sequenced, so as to confirm that the sequence was correct. The plasmid was designated pESCpgkgap-URA-alkS (FIG. 1). In addition, the nucleotide sequence of the alkS gene and the amino acid sequence of the AlkS protein encoded by the gene are shown in SEQ ID NOS: 13 and 14, respectively.

<Construction of Plasmid (pESCpgkgap-HIS-Yfdx) for the Expression of *S. Cerevisiae*-Derived Ferredoxin Gene>

A DNA fragment containing a ferredoxin gene (Yfdx gene) was obtained by PCR using the genomic DNA of *S. cerevisiae* YPH499 as a template. KOD-Plus-Ver.2 (Toyobo Co., Ltd.) was used for PCR. For amplification of the DNA fragment containing the Yfdx gene, the following pair of primers were designed and the composition of the reaction solution and reaction cycle conditions were as follows.

(Primer #1) Yfdx_F2,
(SEQ ID NO: 15)
5'-CACAGGATCCAAAAATGCTGAAAATTGTTACTCGGG-3'

(Primer #2) Yfdx_R2,
(SEQ ID NO: 16)
5'-GGAACTCGAGTTAACTAAAATCGTTGTTATTAACG-3'

[Composition of Reaction Solution]

| | |
|---|---|
| YPH499 genomic DNA (100 ng/µl) | 1 µl |
| 10x buffer for KOD-Plus-Ver.2 | 5 µl |
| 2 mM dNTPs | 5 µl |
| 25 mM MgSO$_4$ | 4 µl |
| Primer #1 (10 µM) | 1.5 µl |
| Primer #2 (10 µM) | 1.5 µl |
| KOD-Plus (1 U/µl) | 1 µl |
| dH$_2$O | 31 µl |
| | 50 µl |

[Reaction Cycle Conditions]

94 degrees C. for 2 minutes-(98 degrees C. for 10 seconds, 55 degrees C. for 30 seconds, 68 degrees C. for 1 minute and 30 seconds)×30 cycles-68 degrees C. for 3 minutes-16 degrees C. stock The PCR product was purified using a QIAquick PCR purification kit (QIAGEN), and then digested with BamH I and Xho I restriction enzymes. After agarose gel electrophoresis, an approximately 0.5-kb fragment was excised, and then purified using a MinElute Gel extraction kit (QIAGEN), thereby obtaining an Insert portion. The pESCpgkgap-HIS plasmid was digested with BamH I and Xho I restriction enzymes. An approximately 7.4-kb fragment was excised, and then purified with a MinElute Gel extraction kit (QIAGEN), thereby obtaining a Vector portion.

Figure 2:
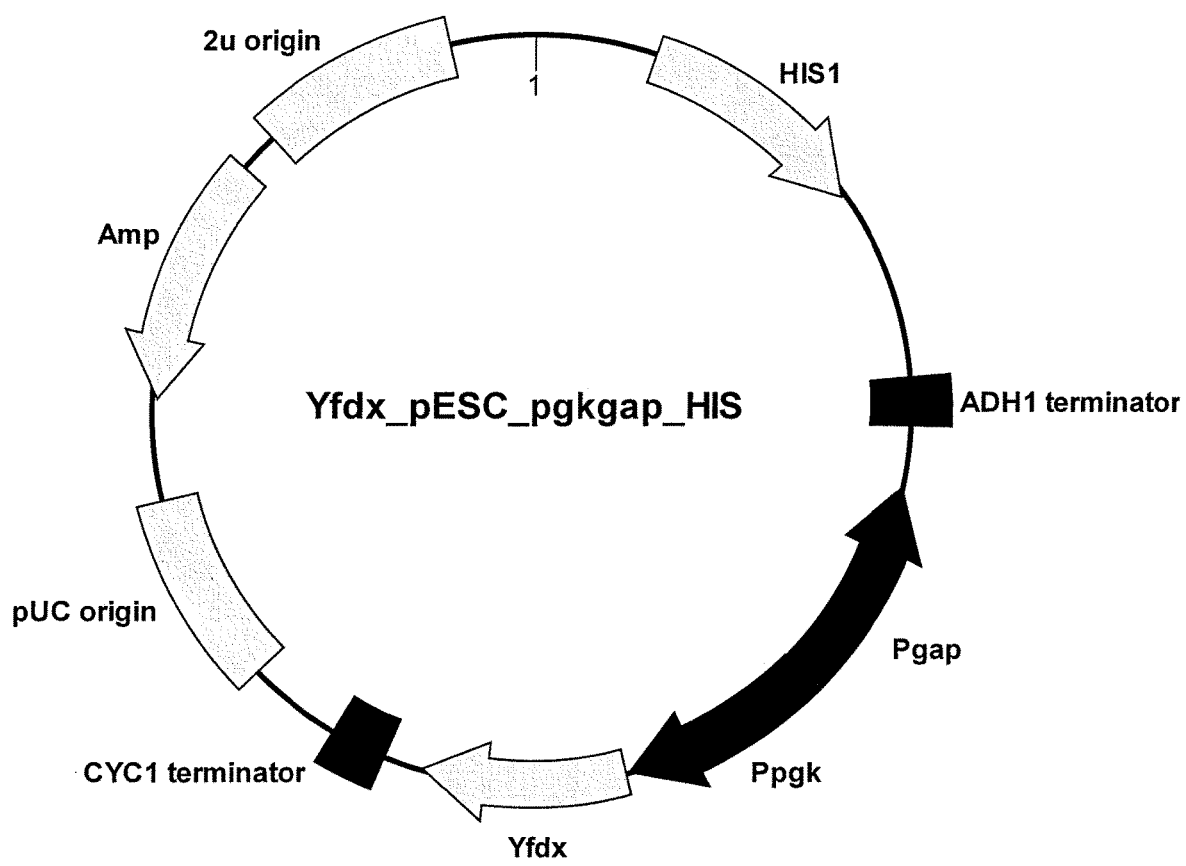
FIG. 2 schematically shows the composition of pESCpg-kgap-HIS-Yfdx.

The above Insert portion and Vector portion were ligated using a Ligation-Convenience Kit (Nippon Gene Co., Ltd.) to transform *Escherichia coli* HST08 (Takara Bio Inc.). Colonies grown on an LB agar medium containing 50 µg/ml ampicillin were cultured in an LB liquid medium containing 50 µg/ml ampicillin, and thus a plasmid was extracted. A QIAprep spin Miniprep Kit (QIAGEN) was used for extraction. The thus obtained plasmid was sequenced to confirm that the sequence was correct and then designated pESCpgkgap-HIS-Yfdx (FIG. 2). In addition, the nucleotide sequence of the Yfdx gene and the amino acid sequence of ferredoxin encoded by the gene are shown in SEQ ID NOS: 1 and 2, respectively.

<Construction of Plasmid (pESCpgkgap-HIS-Yfdr) for the Expression of the *S. cerevisiae*-Derived Ferredoxin NADPH Reductase Gene>

A DNA fragment containing the ferredoxin NADPH reductase gene (Yfdr gene) was obtained by PCR using the genomic DNA of *S. cerevisiae* YPH499 as a template. KOD-Plus-Ver.2 (Toyobo Co., Ltd.) was used for PCR. For amplification of the DNA fragment containing the Yfdr gene, the following pair of primers were designed, and the composition of the reaction solution and reaction cycle conditions were as follows.

(Primer #1) Yfdr_F2,
(SEQ ID NO: 17)
5'-ATATGCGGCCGCAAAAATGAGCTTTGTTCAAATAAGGCAC-3'

(Primer #2) Yfdr_R2,
(SEQ ID NO: 18)
5'-GGCCACTAGTTTATATGCCTTCTACACCGTTCC-3'

[Composition of Reaction Solution]

| | |
|---|---|
| YPH499 genomic DNA (100 ng/µl) | 1 µl |
| 10x buffer for KOD-Plus-Ver.2 | 5 µl |
| 2 mM dNTPs | 5 µl |
| 25 mM MgSO$_4$ | 4 µl |
| Primer #1 (10 µM) | 1.5 µl |
| Primer #2 (10 µM) | 1.5 µl |
| KOD-Plus (1 U/µl) | 1 µl |
| dH$_2$O | 31 µl |
| | 50 µl |

[Reaction Cycle Conditions]

94 degrees C. for 2 minutes-(98 degrees C. for 10 seconds, 55 degrees C. for 30 seconds, 68 degrees C. for 1 minute and 30 seconds)×30 cycles-68 degrees C. for 3 minutes-16 degrees C. stock The PCR product was purified using a QIAquick PCR purification kit (QIAGEN), and then digested with Not I and Spe I restriction enzymes. After agarose gel electrophoresis, an approximately 1.5-kb fragment was excised and then purified using a MinElute Gel extraction kit (QIAGEN), thereby obtaining an Insert portion. The pESCpgkgap-HIS plasmid was digested with Not I and Spe I restriction enzymes. An approximately 7.4-kb fragment was excised and then purified using a MinElute Gel extraction kit (QIAGEN), thereby obtaining a Vector portion.

Figure 3:
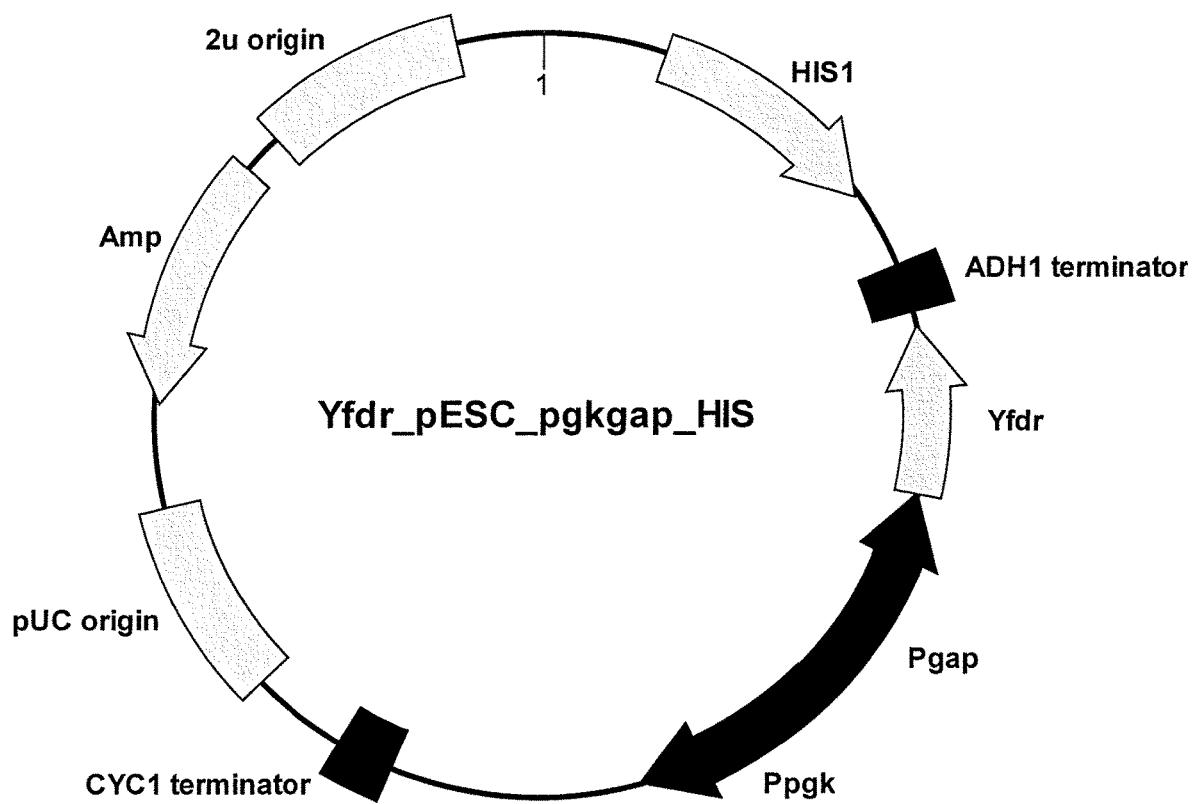
FIG. 3 schematically shows the composition of pESCpg-kgap-HIS-Yfdr.

The above Insert portion and Vector portion were ligated using a Ligation-Convenience Kit (Nippon Gene Co., Ltd.) to transform *Escherichia coli* HST08 (Takara Bio Inc.). Colonies grown on an LB agar medium containing 50 µg/ml ampicillin were cultured in an LB medium containing 50 µg/ml ampicillin to extract a plasmid. A QIAprep spin Miniprep Kit (QIAGEN) was used for extraction. The thus obtained plasmid was sequenced to confirm that the sequence was correct, and thus designated pESCpgkgap-HIS-Yfdr (FIG. 3). In addition, the nucleotide sequence of the Yfdr gene and the amino acid sequence of ferredoxin NADPH reductase encoded by the gene are shown in SEQ ID NOS: 3 and 4, respectively.

<Construction of Plasmid (pESCpgkgap-HIS-YfdxYfdr) for the Co-Expression of Yfdx Gene and Yfdr Gene>

Figure 4:
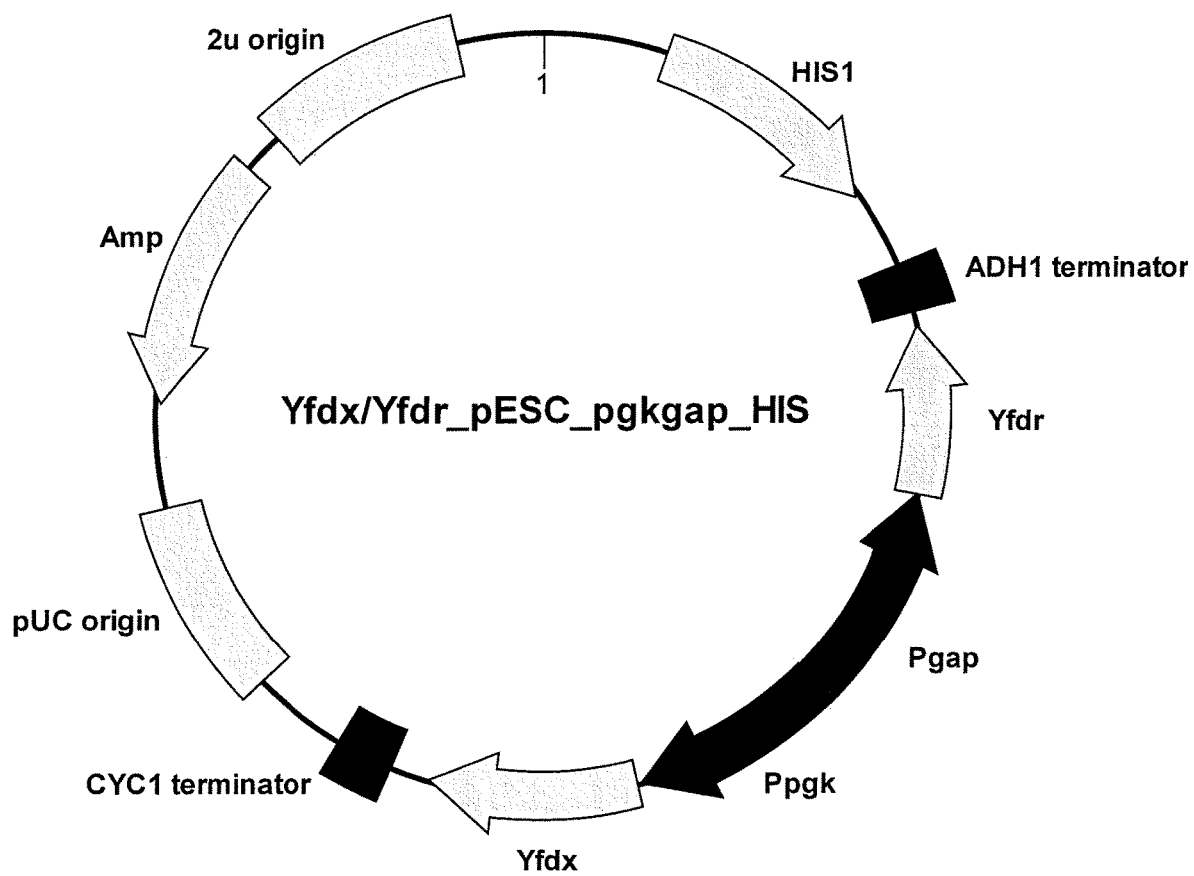
FIG. 4 schematically shows the composition of pESCpg-kgap-HIS-YfdxYfdr.

The pESCpgkgap-HIS-Yfdx plasmid was digested with Not I and Spe I restriction enzymes. An approximately 7.9-kb fragment was excised, and then purified using a MinElute Gel extraction kit (QIAGEN), thereby obtaining a Vector portion. Moreover, the pESCpgkgap-HIS-Yfdr plasmid was digested with Not I and Spe I restriction enzymes. An approximately 1.5-kb fragment was excised and then purified using a MinElute Gel extraction kit (QIAGEN), thereby obtaining an Insert portion. The two above fragments were ligated using a Ligation-Convenience Kit (Nippon Gene Co., Ltd.) to transform *Escherichia coli* HST08 (Takara Bio Inc.). Colonies grown on an LB agar medium containing 50 µg/ml ampicillin were cultured in an LB medium containing 50 µg/ml ampicillin to extract a plasmid. A QIAprep spin Miniprep Kit (QIAGEN) was used for extraction. The thus obtained plasmid was designated pESCpgkgap-HIS-YfdxYfdr (FIG. 4).

<Preparation of *S. cerevisiae* YPH499 Transformant>

The yeast *S. cerevisiae* YPH499 strain was transformed with various expression plasmids constructed as described above. A Frozen Yeast Transformation Kit II (ZymoResearch) was used for transformation according to the manuals provided therewith. Clones grown on SD-Ura,His (BIO101)+adenine hemisulfate agar media were subjected as transformants to the evaluation of alkane productivity. In addition, in this example, the following transformants were prepared: a transformant prepared by introducing the alkS gene using pESCpgkgap-URA-alkS; a transformant prepared by introducing the alkS gene and the ferredoxin gene using pESCpgkgap-URA-alkS and pESCpgkgap-HIS-Yfdx; a transformant prepared by introducing the alkS gene and the ferredoxin NADPH reductase gene using pESCpgkgap-URA-alkS and pESCpgkgap-HIS-Yfdr; and a transformant prepared by introducing the alkS gene, the ferredoxin gene, and the ferredoxin NADPH reductase gene using pESCpgkgap-URA-alkS and pESCpgkgap-HIS-YfdxYfdr/YPH499.

<Evaluation of Alkane Productivity>

The four above prepared types of transformant were separately inoculated into a SD-Ura, His+adenine hemisulfate liquid medium (3 ml) and then cultured at 30 degrees C. for 3 days. A portion of each of the thus obtained culture solutions was inoculated in a SD-Ura, His+adenine hemisulfate liquid medium (5 ml) containing 1 mM Tetradecanal, and then cultured at 30 degrees C. for 3 and 4 days. The culture solution (5 ml) was centrifuged at room temperature and 3000 rpm for 10 minutes to remove the supernatant. The resultant was suspended in 500 µl of a saturated saline solution, and then transferred to a 20-ml vial (Agilent) for GC/MS analysis.

Alkane (Tridecane) biosynthesized from Tetradecanal as a substrate was analyzed and then the productivity thereof was evaluated. In addition, GC/MS analytical conditions are as follows.

<Head Space Sampler Analytical Conditions>

| Head space sampler | | HP7694 (Hewlett-Packard) |
|---|---|---|
| Zone Temp | Oven | 80 degrees C. |
| | Loop | 150 degrees C. |
| | TR.LINE | 200 degrees C. |
| Event Time | GC CYCLE TIME | 10 min |
| | Vial EQ TIME | 15 min |
| | PRESSURIZ. TIME | 0.50 min |
| | Loop Fill TIME | 0.2 min |
| | Loop EQ TIME | 0.2 min |
| | INJECT TIME | 1.00 min |
| Vial Parameter | SHAKE | HIGH |
| Others | Vial pressurization | 15 psi |
| | Loop size | 3 ml |

<GC-MS Analytical Conditions>

| GC/MS | HP6890/5973 GC/MS system (Hewlett-Packard, Wilmington, DE) |
|---|---|
| Column | HP-INNOWAX (Agilent: 19091N-213) |
| Inlet temperature | 260 degrees C. |
| Detector temperature | 260 degrees C. |
| Injection parameter | |
| Split ratio | 1/20 |
| Carrier gas | Helium 1.0 ml/min |
| Oven heating conditions | |
| 60 degrees C. | 1 min |
| Heat at 25 degrees C./min to 260 degrees C. | |
| 260 degrees C. | 1 min |
| PRESSURIZ. TIME | 0.50 min |
| Loop Fill TIME | 0.2 min |
| Loop EQ TIME | 0.2 min |
| INJECT TIME | 1.00 min |
| Vial Parameter | SHAKE | HIGH |

-continued

| Others | Vial pressurization | 15 psi |
|---|---|---|
| | Loop size | 3 ml |

Figure 5:
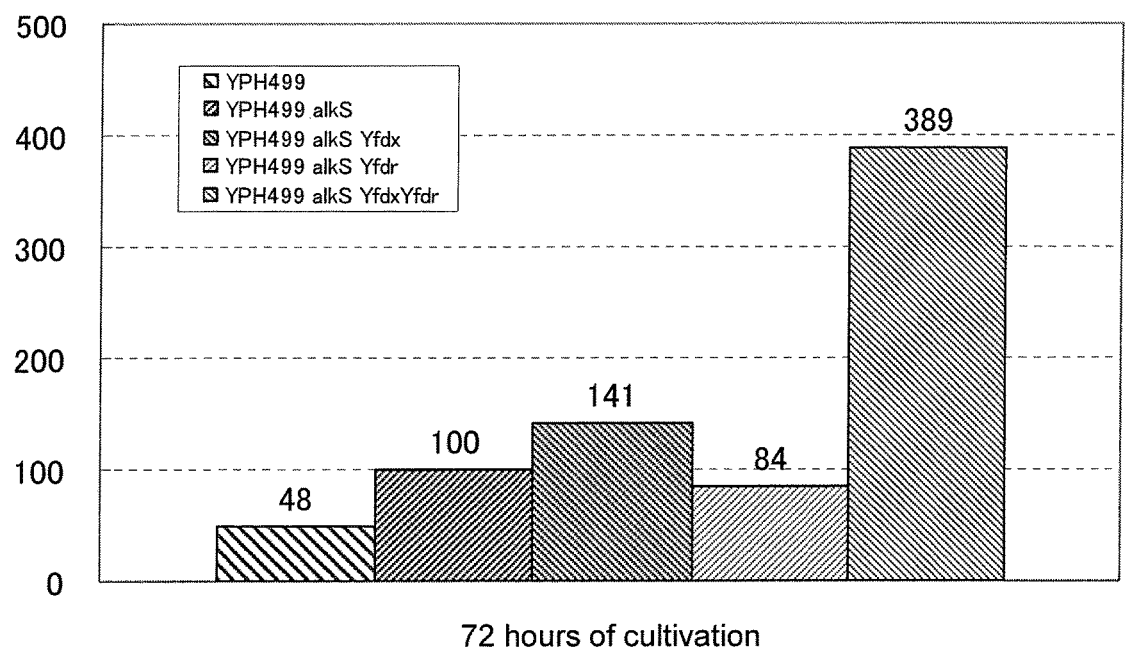
FIG. 5 is a characteristic diagram showing the amounts of alkane (Tridecane) synthesized by various transformants prepared in examples.

The results are shown in FIG. 5. In FIG. 5, the vertical axis indicates the amounts of alkane (Tridecane) synthesized. In FIG. 5, "YPH499" denotes the host before transformation, "YPH499 alkS" denotes the transformant prepared by introducing the alkS gene, "YPH499 alkS Yfdx" denotes the transformant prepared by introducing the alkS gene and the ferredoxin gene, "YPH499 alkS Yfdr" denotes the transformant prepared by introducing the alkS gene and the ferredoxin NADPH reductase gene, and "YPH499 alkS Yfdx Yfdr" denotes the transformant prepared by introducing the alkS gene, the ferredoxin gene and the ferredoxin NADPH reductase gene.

As understood from the results shown in FIG. 5, all transformants in which the alkS gene had been introduced were capable of synthesizing alkane (Tridecane). Furthermore, as shown in FIG. 5, the transformants prepared by introducing the ferredoxin gene had better ability to synthesize alkane than that of the transformants into which no ferredoxin gene had been introduced. Meanwhile, it was understood that the introduction of the ferredoxin NADPH reductase gene alone cannot significantly improve the ability to synthesize alkane. However, it was revealed that the transformant prepared by introducing both the ferredoxin gene and the ferredoxin NADPH reductase gene had the very good ability to synthesize alkane.

Experimental Example 1

In this experimental example, recombinant *Escherichia coli* was prepared by imparting the ability to produce alkane and introducing the ferredoxin gene and/or the ferredoxin NADPH reductase gene, and then the effects of ferredoxin and ferredoxin NADPH reductase on the alkane productivity was confirmed.

<Construction of alkS Expression Plasmid (alkS_pCDF)>

A DNA fragment having an alkane synthase gene (alkS gene) was obtained by PCR using the genomic DNA of *Nostoc* sp. ATCC27437 as a template. KOD-Plus-Ver.2 (Toyobo Co., Ltd.) was used as polymerase for PCR. For amplification of the DNA fragment having the alkS gene, the following pair of primers were designed and the composition of the reaction solution and reaction cycle conditions were as follows.

(Primer #1) alkS_F,
(SEQ ID NO: 19)
5'-GCGCGCGGTACCATGCAGCAGGTTGCAGCCG-3'

(Primer #2) alkS_R,
(SEQ ID NO: 20)
5'-GCGCGCCTCGAGTTAAGCTGCTGTAAGTCCGTAG-3'

[Composition of Reaction Solution]

| *Nostoc* sp. ATCC27437 genomic DNA (100 ng/µl) | 1 µl |
|---|---|
| 10x buffer for KOD-Plus-Ver.2 | 5 µl |
| 2 mM dNTPs | 5 µl |
| 25 mM MgSO$_4$ | 4 µl |
| Primer #1 (10 µM) | 1.5 µl |

| Primer #2 (10 μM) | 1.5 μl |
| KOD-Plus (1 U/μl) | 1 μl |
| dH$_2$O | 31 μl |
| | 50 μl |

[Reaction Cycle Conditions]
94 degrees C. for 2 minutes-(98 degrees C. for 10 seconds, 55 degrees C. for 30 seconds, 68 degrees C. for 1 minute and 30 seconds)×30 cycles-68 degrees C. for 3 minutes-16 degrees C. stock The PCR product was purified using a MinElute PCR purification kit (QIAGEN), and then digested with Kpn I and Xho I restriction enzymes. After agarose gel electrophoresis, an approximately 0.7-kbp fragment was excised and then purified using a MinElute Gel extraction kit (QIAGEN), thereby obtaining an Insert portion. The pCDFDuet-1 plasmid (Novagen) was digested with Kpn I and Xho I restriction enzymes. An approximately 7.4-kb fragment was excised and then purified using a MinElute Gel extraction kit (QIAGEN), thereby obtaining a Vector portion.

Figure 6:
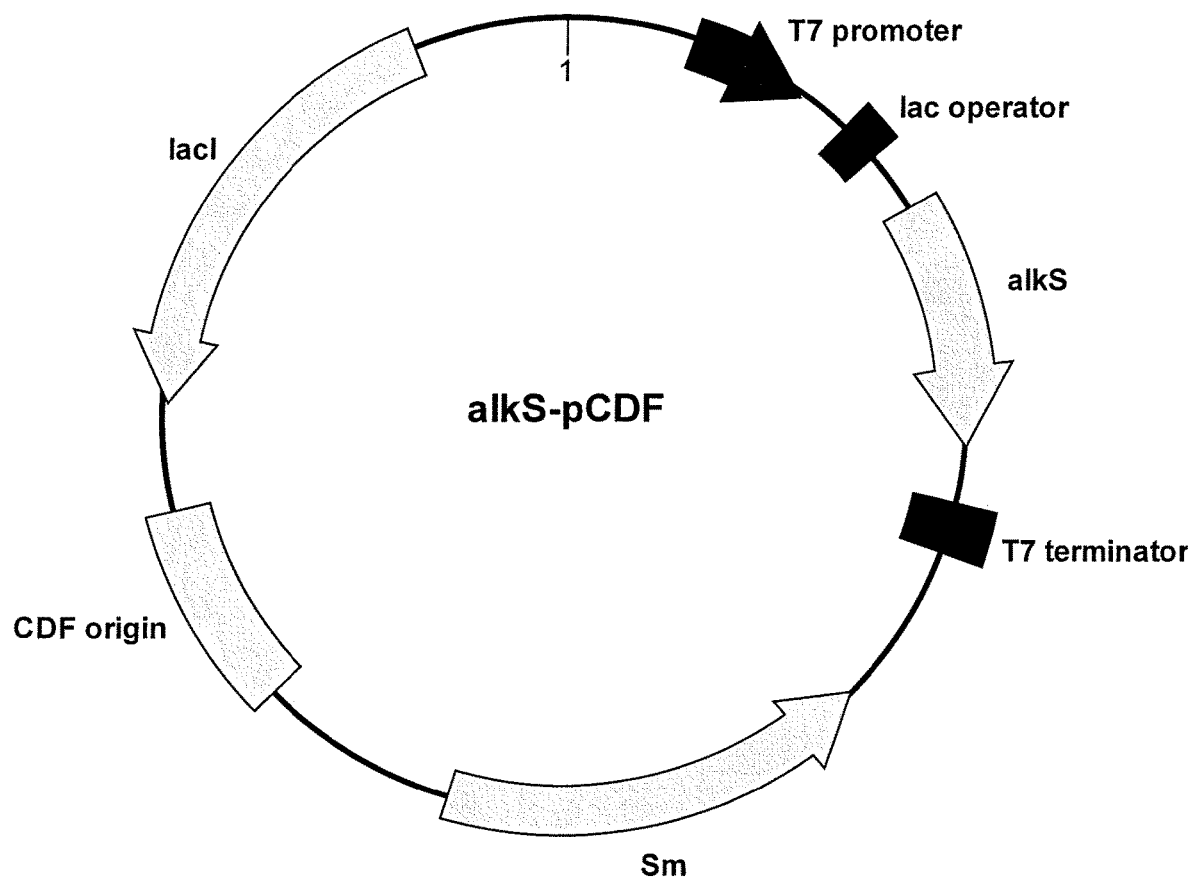
FIG. 6 schematically shows the composition of alkS_p-CDF.

The above Insert portion and Vector portion were ligated using a Ligation-Convenience Kit (Nippon Gene Co., Ltd.) to transform *Escherichia coli* HST08 (Takara Bio Inc.). The thus obtained sequence was sequenced and thus the construction of the target plasmid was confirmed. The thus obtained plasmid was designated alkS_pCDF (FIG. 6).

<Construction of plasmid (Efdx-pCOLA) for the expression of *Escherichia coli* W3110 strain-derived ferredoxin gene>

A DNA fragment having the ferredoxin gene (Efdx) gene was obtained by PCR using the genomic DNA of *Escherichia coli* W3110 as a template. KOD-Plus-Ver.2 (Toyobo Co., Ltd.) was used for PCR. For amplification of the DNA fragment having the Efdx gene, the following pair of primers were designed and the composition of the reaction solution and reaction cycle conditions were as follows.

```
(Primer #1) Efdx_F,
                                   (SEQ ID NO: 21)
5'-GAGATATACATATGCCAAAGATTGTTATTTTGCCTC-3'

(Primer #2) Efdx_R,
                                   (SEQ ID NO: 22)
5'-CAGACTCGAGTTAATGCTCACGCGCATGGTTG-3'
```

[Composition of Reaction Solution]

| W3110 genomic DNA (100 ng/μl) | 1 μl |
| 10x buffer for KOD-Plus-Ver.2 | 5 μl |
| 2 mM dNTPs | 5 μl |
| 25 mM MgSO$_4$ | 4 μl |
| Primer #1 (10 μM) | 1.5 μl |
| Primer #2 (10 μM) | 1.5 μl |
| KOD-Plus (1 U/μl) | 1 μl |
| dH$_2$O | 31 μl |
| | 50 μl |

[Reaction Cycle Conditions]
94 degrees C. for 2 minutes-(98 degrees C. for 10 seconds, 55 degrees C. for 30 seconds, 68 degrees C. for 1 minute and 30 seconds)×30 cycles-68 degrees C. for 3 minutes-4 degrees C. stock The PCR product was purified using a QIAquick PCR purification kit (QIAGEN) and then digested with Nde I and Xho I restriction enzymes. After agarose gel electrophoresis, an approximately 0.4-kb fragment was excised, and then purified using a MinElute Gel extraction kit (QIAGEN), thereby obtaining an Insert portion. The pCOLADuet-1 plasmid (Novagen) was digested with Nde I and Xho I restriction enzymes. An approximately 3.7-kb fragment was excised and then purified using a MinElute Gel extraction kit (QIAGEN), thereby obtaining a Vector portion.

Figure 7:
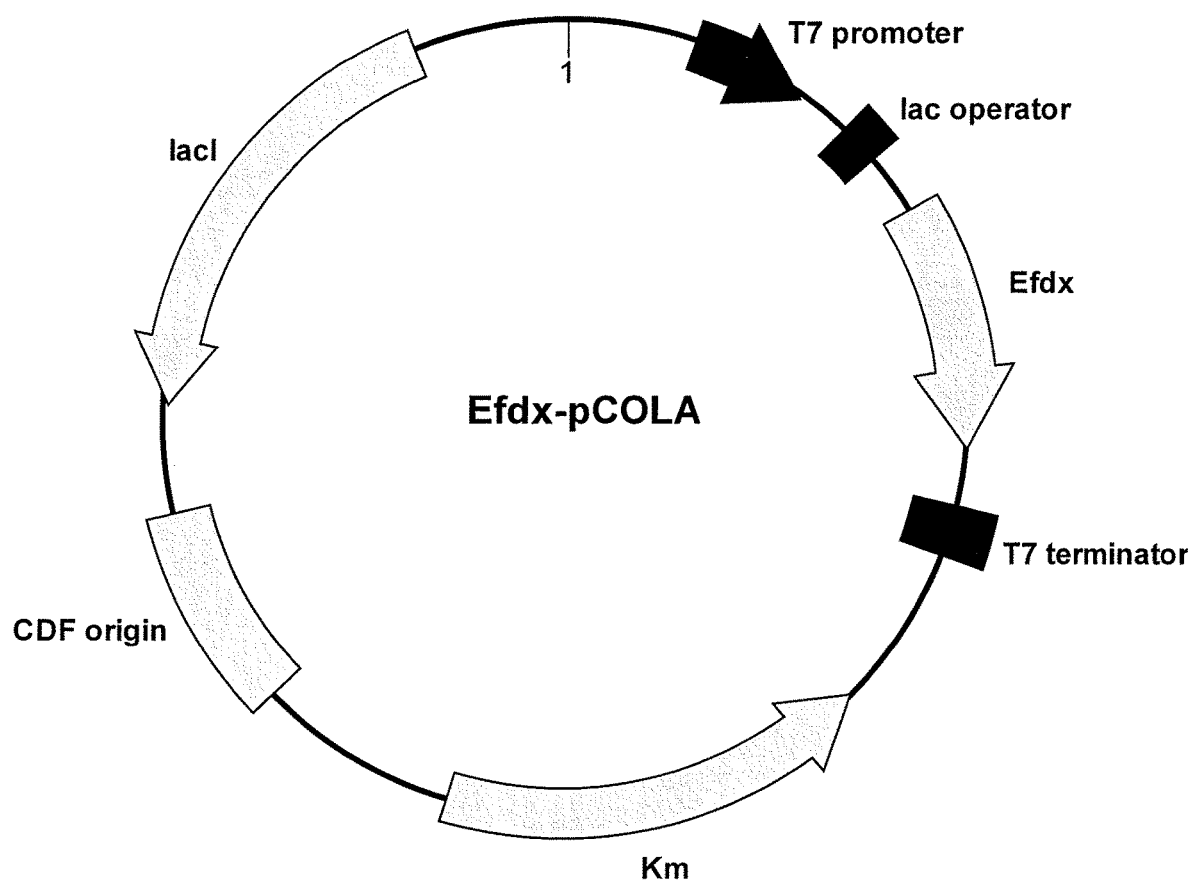
FIG. 7 schematically shows the composition of Efdx-pCOLA.

The above Insert portion and Vector portion were ligated using a Ligation-Convenience Kit (Nippon Gene Co., Ltd.) to transform *Escherichia coli* HST08 (Takara Bio Inc.). Colonies grown on an LB agar medium containing 50 μg/ml ampicillin were cultured in an LB liquid medium containing 50 μg/ml ampicillin to extract a plasmid. A QIAprep spin Miniprep Kit (QIAGEN) was used for extraction. The thus obtained plasmid was sequenced to confirm that the sequence was correct, and then designated Efdx-pCOLA (FIG. 7). In addition, the nucleotide sequence of the Efdx gene and the amino acid sequence of ferredoxin encoded by the gene are shown in SEQ ID NOS: 23 and 24, respectively.

<Construction of Plasmid (Efdr-pCOLA) for the Expression of *Escherichia Coli* W3110 Strain-Derived Ferredoxin NADPH Reductase Gene>

A DNA fragment containing the ferredoxin NADPH reductase (Efdr) gene by PCR using the genomic DNA of *Escherichia coli* W3110 as a template. KOD-Plus-Ver.2 (Toyobo Co., Ltd.) was used for PCR. For amplification of the DNA fragment containing the Efdr gene, the following pair of primers were designed and the composition of the reaction solution and reaction cycle conditions are as follows.

```
(Primer #1) Efdr_F,
                                   (SEQ ID NO: 25)
5'-ATATCCATGGCTGATTGGGTAACAGGC-3'

(Primer #2) Efdr_R,
                                   (SEQ ID NO: 26)
5'-ATTCGGATCCTTACCAGTAATGCTCCGCTGTC-3'
```

[Composition of Reaction Solution]

| W3110 genomic DNA (100 ng/μl) | 1 μl |
| 10x buffer for KOD-Plus-Ver.2 | 5 μl |
| 2 mM dNTPs | 5 μl |
| 25 mM MgSO$_4$ | 4 μl |
| Primer #1 (10 μM) | 1.5 μl |
| Primer #2 (10 μM) | 1.5 μl |
| KOD-Plus (1 U/μl) | 1 μl |
| dH$_2$O | 31 μl |
| | 50 μl |

[Reaction Cycle Conditions]
94 degrees C. for 2 minutes-(98 degrees C. for 10 seconds, 55 degrees C. for 30 seconds, 68 degrees C. for 1 minute and 30 seconds)×30 cycles-68 degrees C. for 3 minutes-4 degrees C. stock The PCR product was purified using a QIAquick PCR purification kit (QIAGEN) and then digested with Nco I and BamH I restriction enzymes. After agarose gel electrophoresis, an approximately 0.8-kb fragment was excised and then purified using a MinElute Gel extraction kit (QIAGEN), thereby obtaining an Insert portion. The pCOLA-Duet-1plasmid (Novagen) was digested with Nco I and BamH I restriction enzymes. An approximately 3.7-kb fragment was excised and then purified using a MinElute Gel extraction kit (QIAGEN), thereby obtaining a Vector portion.

Figure 8:
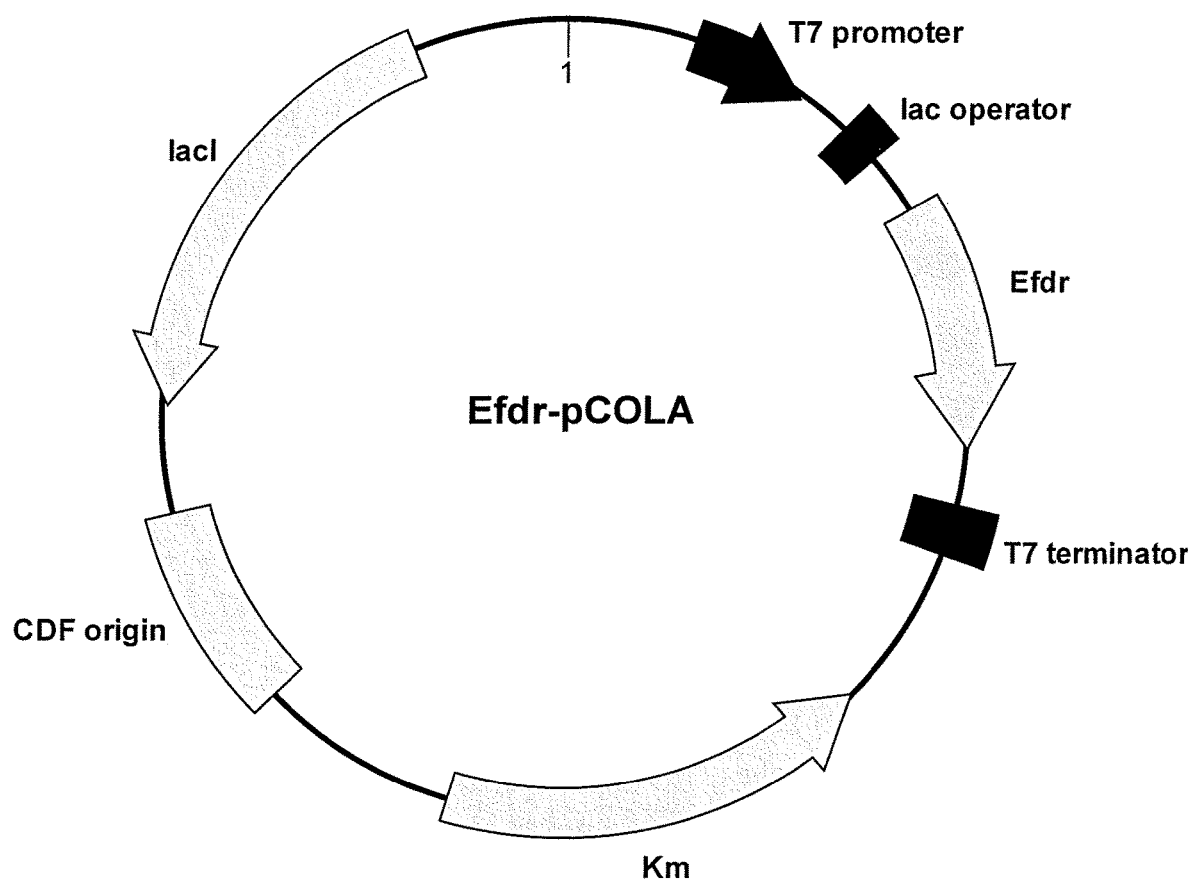
FIG. 8 schematically shows the composition of Efdr-pCOLA.

The above Insert portion and Vector portion were ligated using a Ligation-Convenience Kit (Nippon Gene Co., Ltd.) to transform *Escherichia coli* HST08 (Takara Bio Inc.). Colonies grown on an LB agar medium containing 50 μg/ml ampicillin were cultured in an LB liquid medium containing 50 μg/ml ampicillin to extract a plasmid. A QIAprep spin Miniprep Kit (QIAGEN) was used for extraction. The thus obtained plasmid was sequenced to confirm that the sequence was correct and then designated Efdr-pCOLA (FIG. 8). In addition, the nucleotide sequence of the Efdr gene and the amino acid sequence of ferredoxin encoded by the gene are shown in SEQ ID NOS: 27 and 28, respectively.

<Construction of Plasmid (EfdxEfdr-pCOLA) for the Co-Expression of Efdx Gene and Efdr Gene>

Figure 9:
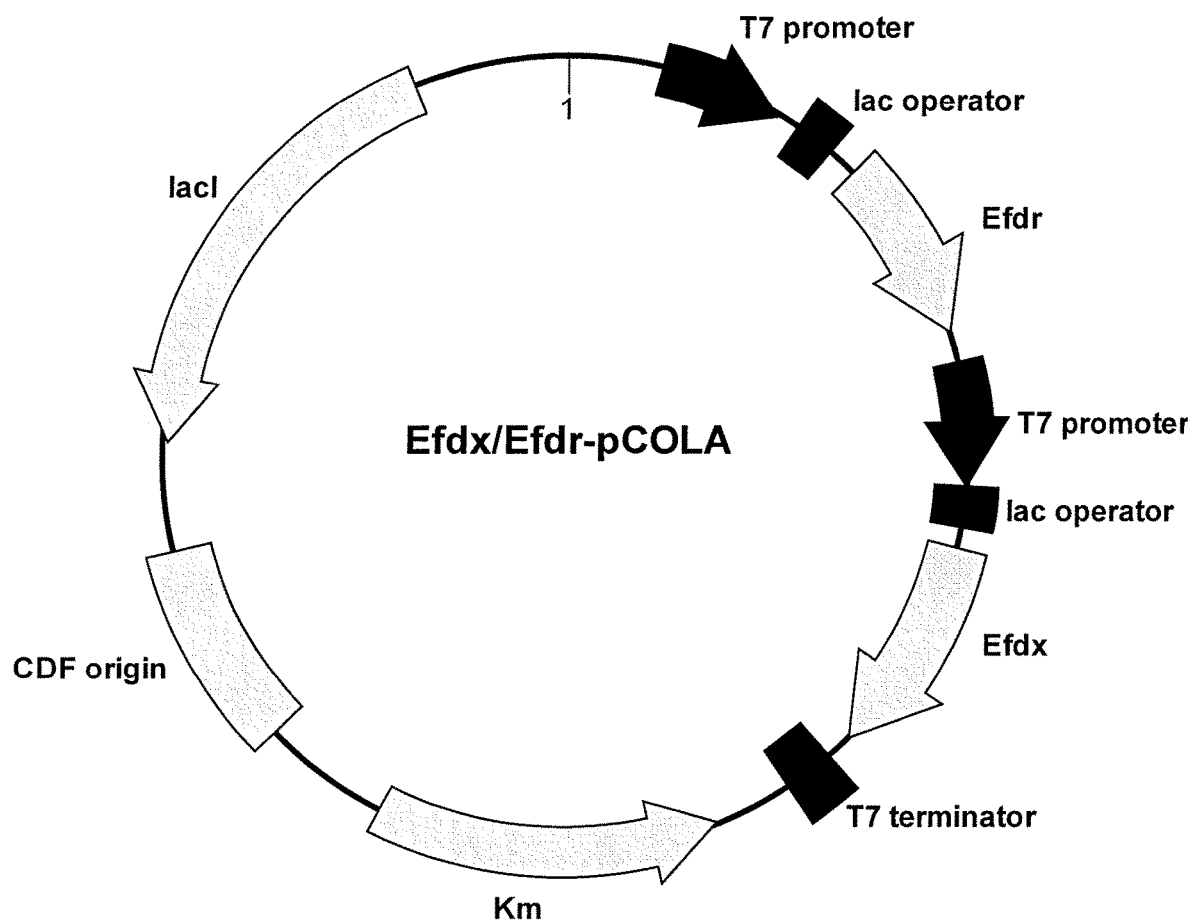
FIG. 9 schematically shows the composition of EfdxEfdr-pCOLA.

The Efdx-pCOLA plasmid was digested with Nco I and BamH I restriction enzymes. An approximately 4.1-kb fragment was excised and then purified using a MinElute Gel extraction kit (QIAGEN), thereby obtaining a Vector portion. Furthermore, the Efdr-pCOLA plasmid was digested with Nco I and BamH I restriction enzymes. An approximately 0.8-kb fragment was excised and then purified using a MinElute Gel extraction kit (QIAGEN), thereby obtaining an Insert portion. The above two fragments were ligated using a Ligation-Convenience Kit (Nippon Gene Co., Ltd.) to transform *Escherichia coli* HST08 (Takara Bio Inc.). Colonies grown on an LB agar medium containing 50 μg/ml ampicillin were cultured in an LB medium containing 50 μg/ml ampicillin to extract a plasmid. A QIAprep spin Miniprep Kit (QIAGEN) was used for extraction. The thus obtained plasmid was designated EfdxEfdr-pCOLA (FIG. 9).

<Preparation of Transformant of *Escherichia coli* BL21 (DE3) Strain>

The *Escherichia coli* BL21 (DE3) strain (Novagen) was transformed using various expression plasmids prepared as described above. Transformation was performed according to the manuals provided therewith. Clones grown on LB agar media containing streptomycin and kanamycin (50 μg/ml each) were subjected as transformants to the evaluation of alkane productivity. In addition, in this example, the following transformants were prepared: a transformant prepared by introducing the alkS gene using alkS_pCDF; a transformant prepared by introducing the alkS gene and the ferredoxin gene using alkS_pCDF and Efdx-pCOLA; a transformant prepared by introducing the alkS gene and the ferredoxin NADPH reductase gene using alkS_pCDF and Efdr-pCOLA, and a transformant prepared by introducing the alkS gene, the ferredoxin gene, and the ferredoxin NADPH reductase gene using alkS_pCDF and EfdxEfdr-pCOLA.

<Evaluation of Alkane Productivity>

The four types of transformants prepared as described above were separately inoculated into 3 mL of LB-Sm, Km (50 μg/ml each) liquid media, and then cultured overnight at 37 degrees C. Each of broth was separately inoculated into 5 mL of LB-Sm, Km (50 μg/ml each) liquid media containing Tetradecanal and 1 mM IPTG and then cultured for 3 and 4 days at 30 degrees C. The culture solutions (5 ml) were centrifuged at room temperature and 3000 rpm for 10 minutes to remove the supernatant. After suspension in a saturated saline solution (500 μl), the resultants were transferred to a 20-ml vial (Agilent) for GC/MS analysis.

Biosynthesized alkane (Tridecane) from Tetradecanal as a substrate was analyzed and the productivity thereof was evaluated. In addition, <head space sampler analytical conditions> and <GC-MS analytical conditions> to be employed for GC/MS analysis are the same as those in Example 1.

Figure 10:
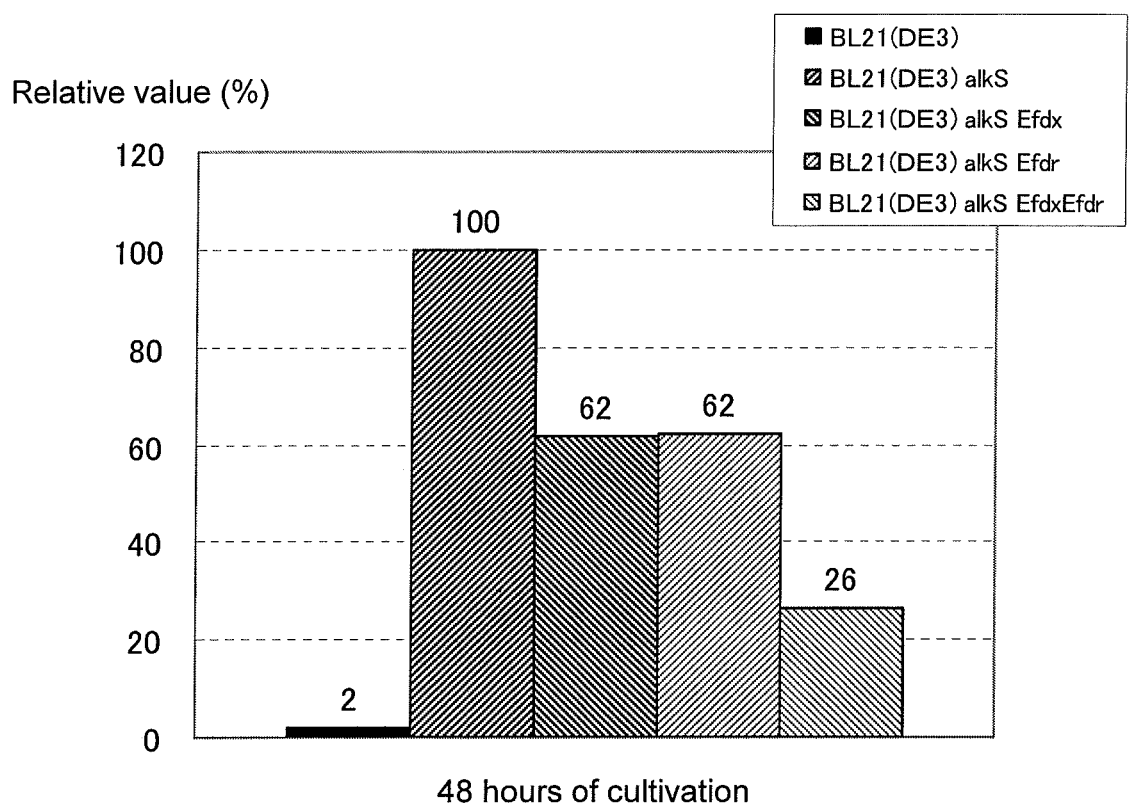
FIG. 10 is a characteristic diagram showing the amounts of alkane (Tridecane) synthesized by various transformants prepared in examples.

The results are shown in FIG. 5. In FIG. 10, the vertical axis indicates the amounts of alkane (Tridecane) synthesized. In FIG. 10, "BL21 (DE3)" represents the host before transformation, "BL21(DE3) alkS" represents the transformant prepared by introducing the alkS gene, "BL21(DE3) alkS Efdx" represents the transformant prepared by introducing the alkS gene and the ferredoxin gene, "BL21(DE3) alkS Efdr" represents the transformant prepared by introducing the alkS gene and the ferredoxin NADPH reductase gene, and "BL21(DE3) alkS Efdx Efdr" represents the transformant prepared by introducing the alkS gene, the ferredoxin gene, and the ferredoxin NADPH reductase gene.

It was understood from the results shown in FIG. 10, all transformants prepared by introducing the alkS gene had the ability to synthesize alkane (Tridecane). However, as shown in FIG. 10, further introduction of the ferredoxin gene and the ferredoxin NADPH reductase gene did not result in improved ability to synthesize alkane.

The invention claimed is:

1. A method for producing alkane, comprising culturing recombinant yeast capable of synthesizing alkane, in which an alkane synthase gene, a ferredoxin gene, and a ferredoxin NADPH reductase gene have been introduced, in a medium and then producing alkane in the medium, wherein the yeast is *Saccharomyces cerevisiae*, wherein said ferredoxin gene encodes a protein comprising the amino acid sequence of SEQ ID NO: 2, or encodes a protein comprising an amino acid sequence having 90% or more identity with the amino acid sequence of SEQ ID NO: 2 and having ferredoxin activity, wherein said ferredoxin NADPH reductase gene encodes a protein comprising the amino acid sequence of SEQ ID NO: 4, or encodes a protein comprising an amino acid sequence having 90% or more identity with the amino acid sequence of SEQ ID NO: 4 and having ferredoxin NADPH reductase activity, and wherein said alkane synthase gene is an alkS gene from *Nostoc* sp.

2. The method for producing alkane according to claim 1, wherein the alkane synthase has activity to convert aldehyde into alkane.

3. The method for producing alkane according to claim 1, wherein $C_{9-16}$ alkane is produced.

4. A recombinant yeast capable of synthesizing alkane, wherein an alkane synthase gene, a ferredoxin gene, and a ferredoxin NADPH reductase gene have been introduced, wherein the yeast is *Saccharomyces cerevisiae*, wherein said ferredoxin gene encodes a protein comprising the amino acid sequence of SEQ ID NO: 2, or encoded a protein comprising an amino acid sequence having 90% or more identity with the amino acid sequence of SEQ ID NO: 2 and having ferredoxin activity, wherein said ferredoxin NADPH reductase gene encodes a protein comprising the amino acid sequence of SEQ ID NO: 4, or encodes a protein comprising an amino acid sequence having 90% or more identity with the amino acid sequence of SEQ ID NO: 4 and having ferredoxin NADPH reductase activity, and wherein said alkane synthase gene is an alkS gene from *Nostoc* sp.

\* \* \* \* \*